US010620214B2

United States Patent
Kritzer et al.

(10) Patent No.: US 10,620,214 B2
(45) Date of Patent: Apr. 14, 2020

(54) CHLOROALKANE PENETRATION METHOD FOR QUANTIFYING ACCESS OF A MOLECULE INTO A CELL

(71) Applicant: TRUSTEES OF TUFTS COLLEGE, Medford, MA (US)

(72) Inventors: Joshua Kritzer, Medford, MA (US); Leila Peraro, Medford, MA (US)

(73) Assignee: TRUSTEES OF TUFTS COLLEGE, Medford, MA (US)

( * ) Notice: Subject to any disclaimer, the term of this patent is extended or adjusted under 35 U.S.C. 154(b) by 0 days.

(21) Appl. No.: 15/818,282

(22) Filed: Nov. 20, 2017

(65) Prior Publication Data

US 2018/0188260 A1 Jul. 5, 2018

Related U.S. Application Data

(60) Provisional application No. 62/424,955, filed on Nov. 21, 2016.

(51) Int. Cl.
| | | |
|---|---|---|
| C12Q 1/32 | (2006.01) | |
| C12N 9/06 | (2006.01) | |
| G01N 33/58 | (2006.01) | |
| C12N 9/04 | (2006.01) | |

(52) U.S. Cl.
CPC ......... *G01N 33/582* (2013.01); *C12N 9/0006* (2013.01); *C12Q 1/32* (2013.01); *C07K 2319/00* (2013.01)

(58) Field of Classification Search
None
See application file for complete search history.

(56) References Cited

PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Ballister et al. Nat Commun. Nov. 17, 2014;5:5475 (Year: 2014).*
Los et al. ACS Chem Biol. Jun. 20, 2008;3(6):373-82 (Year: 2008).*
Friedman et al. Science. Oct. 21, 2011;334(6054):358-62 (Year: 2011).*

* cited by examiner

*Primary Examiner* — Christian L Fronda
(74) *Attorney, Agent, or Firm* — Melissa Hunter-Ensor; Leslie Serunian; Greenberg Traurig, LLP

(57) ABSTRACT

As described below, the invention provides methods for localizing and quantifying the extent to which a molecule penetrates a cell.

9 Claims, 17 Drawing Sheets
Specification includes a Sequence Listing.

SEQUENCE LISTING

<160> NUMBER OF SEQ ID NOS: 5

<210> SEQ ID NO 1
<211> LENGTH: 297
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 1

Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Glu Ile Ser Gly
    290                 295

<210> SEQ ID NO 2
<211> LENGTH: 891
<212> TYPE: DNA
<213> ORGANISM: Artificial Sequence
<220> FEATURE:
<223> OTHER INFORMATION: Description of Artificial Sequence: Synthetic
      polypeptide

<400> SEQUENCE: 2
atggcagaaa tcggtactgg ctttccattc gaccccatt  atgtggaagt cctgggcgag      60
cgcatgcact acgtcgatgt tggtccgcgc gatggcaccc ctgtgctgtt cctgcacggt     120
aacccgacct cctcctacgt gtggcgcaac atcatcccgc atgttgcacc gacccatcgc     180
```

```
tgcattgctc cagacctgat cggtatgggc aaatccgaca aaccagacct gggttatttc    240
ttcgacgacc acgtccgctt catggatgcc ttcatcgaag ccctgggtct ggaagaggtc    300
gtcctggtca ttcacgactg gggctccgct ctgggtttcc actgggccaa gcgcaatcca    360
gagcgcgtca aggtattgca atttatggag ttcatccgcc ctatcccgac ctgggacgaa    420
tggccagaat tgcccgcga gaccttccag gccttccgca ccaccgacgt cggccgcaag    480
ctgatcatcg atcagaacgt ttttatcgag ggtacgctgc cgatgggtgt cgtccgcccg    540
ctgactgaag tcgagatgga ccattaccgc gagccgttcc tgaatcctgt tgaccgcgag    600
ccactgtggc gcttcccaaa cgagctgcca atcgccggtg agccagcgaa catcgtcgcg    660
ctggtcgaag aatacatgga ctggctgcac cagtcccctg tcccgaagct gctgttctgg    720
ggcaccccag gcgttctgat cccaccggcc gaagccgctc gcctggccaa agcctgcct    780 aactgcaagg ctgtggacat cggcccgggt ctgaatctgc tgcaagaaga caacccggac    840
ctgatcggca gcgagatcgc gcgctggctg tcgacgctcg agatttccgg c           891
```

<210> SEQ ID NO 3
<211> LENGTH: 887
<212> TYPE: PRT
<213> ORGANISM: Artificial Sequence
<220> FEATURE:
<223> OTHER INFORMATION: Description of Artificial Sequence: Synthetic
     polypeptide <400> SEQUENCE: 3

```
Met Ala Glu Ile Gly Thr Gly Phe Pro Phe Asp Pro His Tyr Val Glu
1               5                  10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
```

-continued

```
                225                 230                 235                 240
        Gly Thr Pro Gly Val Leu Ile Pro Pro Ala Glu Ala Ala Arg Leu Ala
                        245                 250                 255
        Lys Ser Leu Pro Asn Cys Lys Ala Val Asp Ile Gly Pro Gly Leu Asn
                        260                 265                 270
        Leu Leu Gln Glu Asp Asn Pro Asp Leu Ile Gly Ser Glu Ile Ala Arg
                        275                 280                 285
        Trp Leu Ser Thr Leu Glu Ile Ser Gly Tyr Thr Met Val Ser Lys Gly
                290                 295                 300
        Ala Glu Leu Phe Thr Gly Ile Val Pro Ile Leu Ile Glu Leu Asn Gly
        305                 310                 315                 320
        Asp Val Asn Gly His Lys Phe Ser Val Ser Gly Glu Gly Glu Gly Asp
                        325                 330                 335
        Ala Thr Tyr Gly Lys Leu Thr Leu Lys Phe Ile Cys Thr Thr Gly Lys
                        340                 345                 350
        Leu Pro Val Pro Trp Pro Thr Leu Val Thr Thr Leu Ser Tyr Gly Val
                        355                 360                 365
        Gln Cys Phe Ser Arg Tyr Pro Asp His Met Lys Gln His Asp Phe Phe
                370                 375                 380
        Lys Ser Ala Met Pro Glu Gly Tyr Ile Gln Glu Arg Thr Ile Phe Phe
        385                 390                 395                 400
        Glu Asp Asp Gly Asn Tyr Lys Ser Arg Ala Glu Val Lys Phe Glu Gly
                        405                 410                 415
        Asp Thr Leu Val Asn Arg Ile Glu Leu Thr Gly Thr Asp Phe Lys Glu
                        420                 425                 430
        Asp Gly Asn Ile Leu Gly Asn Lys Met Glu Tyr Asn Tyr Asn Ala His
                        435                 440                 445
        Asn Val Tyr Ile Met Thr Asp Lys Ala Lys Asn Gly Ile Lys Val Asn
                        450                 455                 460
        Phe Lys Ile Arg His Asn Ile Glu Asp Gly Ser Val Gln Leu Ala Asp
        465                 470                 475                 480
        His Tyr Gln Gln Asn Thr Pro Ile Gly Asp Gly Pro Val Leu Leu Pro
                        485                 490                 495
        Asp Asn His Tyr Leu Ser Thr Gln Ser Ala Leu Ser Lys Asp Pro Asn
                        500                 505                 510
        Glu Lys Arg Asp His Met Ile Tyr Phe Gly Phe Val Thr Ala Ala Ala
                        515                 520                 525
        Ile Thr His Gly Met Asp Glu Leu Tyr Lys Ser Gly Leu Arg Ser Arg
                530                 535                 540
        Val Met Ser Lys Gly Thr Ser Ser Asp Thr Ser Leu Gly Arg Val Ser
        545                 550                 555                 560
        Arg Ala Ala Phe Pro Ser Pro Thr Ala Ala Glu Met Ala Glu Ile Ser
                        565                 570                 575
        Arg Ile Gln Tyr Glu Met Glu Tyr Thr Glu Gly Ile Ser Gln Arg Met
                        580                 585                 590
        Arg Val Pro Glu Lys Leu Lys Val Ala Pro Pro Asn Ala Asp Leu Glu
                        595                 600                 605
        Gln Gly Phe Gln Glu Gly Val Pro Asn Ala Ser Val Ile Met Gln Val
                        610                 615                 620
        Pro Glu Arg Ile Val Val Ala Gly Asn Asn Glu Asp Val Ser Phe Ser
        625                 630                 635                 640
        Arg Pro Ala Asp Leu Asp Leu Ile Gln Ser Thr Pro Phe Lys Pro Leu
                        645                 650                 655
```

Ala Leu Lys Thr Pro Pro Arg Val Leu Thr Leu Ser Glu Arg Pro Leu
            660                 665                 670

Asp Phe Leu Asp Leu Glu Arg Pro Thr Thr Pro Gln Asn Glu Glu
        675                 680                 685

Ile Arg Ala Val Gly Arg Leu Lys Arg Glu Arg Ser Met Ser Glu Asn
690                 695                 700

Ala Val Arg Gln Asn Gly Gln Leu Val Arg Asn Asp Ser Leu Trp His
705                 710                 715                 720

Arg Ser Asp Ser Ala Pro Arg Asn Lys Ile Ser Arg Phe Gln Ala Pro
                725                 730                 735

Ile Ser Ala Pro Glu Tyr Thr Val Thr Pro Ser Pro Gln Ala Arg
            740                 745                 750

Val Cys Pro Pro His Met Leu Pro Glu Asp Gly Ala Asn Leu Ser Ser
                755                 760                 765

Ala Arg Gly Ile Leu Ser Leu Ile Gln Ser Ser Thr Arg Arg Ala Tyr
770                 775                 780

Gln Gln Ile Leu Asp Val Leu Asp Glu Asn Arg Arg Pro Val Leu Arg
785                 790                 795                 800

Gly Gly Ser Ala Ala Thr Ser Asn Pro His His Asp Asn Val Arg
                805                 810                 815

Tyr Gly Ile Ser Asn Ile Asp Thr Thr Ile Glu Gly Thr Ser Asp Asp
            820                 825                 830

Leu Thr Val Val Asp Ala Ala Ser Leu Arg Arg Gln Ile Ile Lys Leu
        835                 840                 845

Asn Arg Arg Leu Gln Leu Leu Glu Glu Glu Asn Lys Glu Arg Ala Lys
            850                 855                 860

Arg Glu Met Val Met Tyr Ser Ile Thr Val Ala Phe Trp Leu Leu Asn
865                 870                 875                 880

Ser Trp Leu Trp Phe Arg Arg
                885

<210> SEQ ID NO 4
<211> LENGTH: 6615
<212> TYPE: DNA
<213> ORGANISM: Artificial Sequence
<220> FEATURE:
<223> OTHER INFORMATION: Description of Artificial Sequence: Synthetic
      polypeptide

<400> SEQUENCE: 4
catgcattag ttattaatag taatcaatta cggggtcatt agttcatagc ccatatatgg    60
agttccgcgt tacataactt acggtaaatg gcccgcctgg ctgaccgccc aacgaccccc   120
gcccattgac gtcaataatg acgtatgttc ccatagtaac gccaataggg actttccatt   180
gacgtcaatg ggtggagtat ttacggtaaa ctgcccactt ggcagtacat caagtgtatc   240
atatgccaag tacgccccct attgacgtca atgacggtaa atggcccgcc tggcattatg   300
cccagtacat gaccttatgg gactttccta cttggcagta catctacgta ttagtcatcg   360
ctattaccat ggtgatgcgg ttttggcagt acatcaatgg gcgtggatag cggtttgact   420
cacggggatt tccaagtctc cacccattg acgtcaatg gagtttgttt tggcaccaaa   480
atcaacggga ctttccaaaa tgtcgtaaca actccgcccc attgacgcaa atgggcggta   540
ggcgtgtacg gtgggaggtc tatataagca gagctggttt agtgaaccgt cagatccgct   600
agcgctaccg gtcgccatgg cagaaatcgg tactggcttt ccattcgacc ccattatgt   660

```
ggaagtcctg ggcgagcgca tgcactacgt cgatgttggt ccgcgcgatg gcacccctgt    720
gctgttcctg cacggtaacc cgacctcctc ctacgtgtgg cgcaacatca tcccgcatgt    780
tgcaccgacc catcgctgca ttgctccaga cctgatcggt atgggcaaat ccgacaaacc    840
agacctgggt tatttcttcg acgaccacgt ccgcttcatg gatgccttca tcgaagccct    900
gggtctggaa gaggtcgtcc tggtcattca cgactggggc tccgctctgg gtttccactg    960
ggccaagcgc aatccagagc gcgtcaaagg tattgcattt atggagttca tccgccctat   1020
cccgacctgg gacgaatggc cagaatttgc ccgcgagacc ttccaggcct tccgcaccac   1080
cgacgtcggc cgcaagctga tcatcgatca gaacgttttt atcgagggta cgctgccgat   1140
gggtgtcgtc cgcccgctga ctgaagtcga gatggaccat taccgcgagc cgttcctgaa   1200
tcctgttgac cgcgagccac tgtggcgctt cccaaacgag ctgccaatcg ccggtgagcc   1260
agcgaacatc gtcgcgctgg tcgaagaata catggactgg ctgcaccagt cccctgtccc   1320
gaagctgctg ttctgggggca ccccaggcgt tctgatccca ccggccgaag ccgctcgcct   1380
ggccaaaagc ctgcctaact gcaaggctgt ggacatcggc ccgggtctga atctgctgca   1440
agaagacaac ccggacctga tcggcagcga gatcgcgcgc tggctgtcga cgctcgagat   1500
ttccggttac accatggtga gcaagggcgc cgagctgttc accggcatcg tgcccatcct   1560
gatcgagctg aatggcgatg tgaatggcca caagttcagc gtgagcggcg agggcgaggg   1620
cgatgccacc tacggcaagc tgaccctgaa gttcatctgc accaccggca agctgcctgt   1680
gccctggccc accctggtga ccaccctgag ctacggcgtg cagtgcttct cacgctaccc   1740
cgatcacatg aagcagcacg acttcttcaa gagcgccatg cctgagggct acatccagga   1800
gcgcaccatc ttcttcgagg atgacggcaa ctacaagtcg cgcgccgagg tgaagttcga   1860
gggcgatacc ctggtgaatc gcatcgagct gaccggcacc gatttcaagg aggatggcaa   1920
catcctgggc aataagatgg agtacaacta caacgcccac aatgtgtaca tcatgaccga   1980
caaggccaag aatggcatca aggtgaactt caagatccgc cacaacatcg aggatggcag   2040
cgtgcagctg gccgaccact accagcagaa taccccccatc ggcgatggcc ctgtgctgct   2100
gcccgataac cactacctgt ccaccccgag cgccctgtcc aaggaccccca acgagaagcg   2160 cgatcacatg atctacttcg gcttcgtgac cgccgccgcc atcacccacg gcatggatga   2220
gctgtacaag tccggactca gatctcgagt gatgagtaaa ggaacaagca gtgacacatc   2280
actaggaagg gtgagcaggg cagcatttcc ttctcccact gctgctgaga tggcagaaat   2340
tagtcgaatt cagtacgaaa tggaatatac tgaaggcatt agtcagcgaa tgagggtccc   2400
agaaaagtta aaagtagcac cgccaaacgc tgacctggaa caaggattcc aagaaggagt   2460
tccaaatgct agtgtgataa tgcaagttcc ggagaggatt gttgtagcag gaaataatga   2520
agatgtttca ttttcaagac cagcagatct tgaccttatt cagtcaactc cctttaaacc   2580
cctggcactg aaaacaccac ctcgtgtact tacgctgagt gaaagaccac tagattttct   2640
ggatttagaa agacctccta caaccccctca aaatgaagaa atccgagcag ttggcagact   2700
aaaaagagag cggtctatga gtgaaaatgc tgttcgccaa aatggacagc tggtcagaaa   2760
tgattctctg tggcacagat cagattctgc cccaagaaat aaaatttcaa ggttccaggc   2820
accgatttct gcaccggagt acactgtgac accatcgcca caacaggctc gggtctgtcc   2880
tccccatatg ttacctgaag atggagctaa tctttcctct gctcgtggca ttttgtcgct   2940
tatccagtct tctactcgta gggcatacca gcagatcttg gatgtgctgg atgaaaatcg   3000
cagacctgtg ttgcgtggtg ggtctgctgc cgccacttct aatcctcatc atgacaacgt   3060
```

```
caggtatggc atttcaaata tagatacaac cattgaagga acgtcagatg acctgactgt    3120
tgtagatgca gcttcactaa gacgacagat aatcaaacta aatagacgtc tacaacttct    3180
ggaagaggag aacaaagaac gtgctaaaag agaaatggtc atgtattcaa ttactgtagc    3240
tttctggctg cttaatagct ggctctggtt tcgccgctag ggatccaccg gatctagata    3300
actgatcata atcagccata ccacatttgt agaggtttta cttgctttaa aaaacctccc    3360
acacctcccc ctgaacctga aacataaaat gaatgcaatt gttgttgtta acttgtttat    3420
tgcagcttat aatggttaca aataaagcaa tagcatcaca aatttcacaa ataaagcatt    3480 ttttcactg cattctagtt gtggtttgtc caaactcatc aatgtatctt aacgcgtaaa     3540
ttgtaagcgt taatattttg ttaaaattcg cgttaaattt ttgttaaatc agctcatttt    3600
ttaaccaata ggccgaaatc ggcaaaatcc cttataaatc aaaagaatag accgagatag    3660
ggttgagtgt tgttccagtt tggaacaaga gtccactatt aaagaacgtg gactccaacg    3720
tcaaagggcg aaaaaccgtc tatcagggcg atggcccact acgtgaacca tcaccctaat    3780
caagtttttt ggggtcgagg tgccgtaaag cactaaatcg gaaccctaaa gggagccccc    3840
gatttagagc ttgacgggga aagccggcga acgtggcgag aaaggaaggg aagaaagcga    3900
aaggagcggg cgctagggcg ctggcaagtg tagcggtcac gctgcgcgta accaccacac    3960
ccgccgcgct taatgcgccg ctacaggcg cgtcaggtgg cacttttcgg ggaaatgtgc     4020 gcggaaccc tatttgttta tttttctaaa tacattcaaa tatgtatccg ctcatgagac     4080
aataaccctg ataaatgctt caataatatt gaaaaaggaa gagtcctgag gcggaaagaa    4140
ccagctgtgg aatgtgtgtc agttagggtg tggaaagtcc ccaggctccc cagcaggcag    4200
aagtatgcaa agcatgcatc tcaattagtc agcaaccagg tgtggaaagt ccccaggctc    4260
cccagcaggc agaagtatgc aaagcatgca tctcaattag tcagcaacca tagtcccgcc    4320
cctaactccg cccatcccgc cctaactccg cccagttcc gcccattctc cgccccatgg     4380
ctgactaatt ttttttattt atgcagaggc cgaggccgcc tcggcctctg agctattcca    4440
gaagtagtga ggaggctttt ttggaggcct aggcttttgc aaagatcgat caagagacag    4500
gatgaggatc gtttcgcatg attgaacaag atggattgca cgcaggttct ccggccgctt    4560
gggtggagag gctattcggc tatgactggg cacaacagac aatcggctgc tctgatgccg    4620
ccgtgttccg gctgtcagcg caggggcgcc cggttctttt tgtcaagacc gacctgtccg    4680
gtgccctgaa tgaactgcaa gacgaggcag cgcggctatc gtggctggcc acgacgggcg    4740
ttccttgcgc agctgtgctc gacgttgtca ctgaagcggg aagggactgg ctgctattgg    4800
gcgaagtgcc ggggcaggat ctcctgtcat ctcaccttgc tcctgccgag aaagtatcca    4860
tcatggctga tgcaatgcgg cggctgcata cgcttgatcc ggctacctgc ccattcgacc    4920
accaagcgaa acatcgcatc gagcgagcac gtactcggat ggaagccggt cttgtcgatc    4980
aggatgatct ggacgaagag catcagggc tcgcgccagc cgaactgttc gccaggctca     5040
aggcgagcat gcccgacggc gaggatctcg tcgtgaccca tggcgatgcc tgcttgccga    5100
atatcatggt ggaaaatggc cgcttttctg gattcatcga ctgtggccgg ctgggtgtgg    5160
cggaccgcta tcaggacata gcgttggcta cccgtgatat tgctgaagag cttggcggcg    5220
aatgggctga ccgcttcctc gtgctttacg gtatcgccgc tcccgattcg cagcgcatcg    5280
ccttctatcg ccttcttgac gagttcttct gagcgggact ctggggttcg aaatgaccga    5340
ccaagcgacg cccaacctgc catcacgaga tttcgattcc accgccgcct tctatgaaag    5400
```

```
gttgggcttc ggaatcgttt tccgggacgc cggctggatg atcctccagc gcggggatct      5460
catgctggag ttcttcgccc accctagggg gaggctaact gaaacacgga aggagacaat      5520
accggaagga acccgcgcta tgacggcaat aaaaagacag aataaaacgc acggtgttgg      5580
gtcgtttgtt cataaacgcg gggttcggtc ccagggctgg cactctgtcg atacccacc       5640 gagacccat tggggccaat acgccgcgt ttcttcctttt tccccacccc accccccaag       5700
ttcgggtgaa ggcccagggc tcgcagccaa cgtcggggcg gcaggccctg ccatagcctc      5760
aggttactca tatatacttt agattgattt aaaacttcat ttttaattta aaaggatcta      5820
ggtgaagatc cttttgata atctcatgac caaaatccct taacgtgagt tttcgttcca      5880
ctgagcgtca gacccgtag aaaagatcaa aggatcttct tgagatcctt tttttctgcg       5940
cgtaatctgc tgcttgcaaa caaaaaaacc accgctacca gcggtggttt gtttgccgga      6000
tcaagagcta ccaactcttt ttccgaaggt aactggcttc agcagagcgc agataccaaa      6060
tactgttctt ctagtgtagc cgtagttagg ccaccacttc aagaactctg tagcaccgcc      6120 tacataccctc gctctgctaa tcctgttacc agtggctgct gccagtggcg ataagtcgtg     6180
tcttaccggg ttggactcaa gacgatagtt accggataag gcgcagcggt cgggctgaac      6240 gggggggttcg tgcacacagc ccagcttgga gcgaacgacc tacaccgaac tgagatacct    6300
acagcgtgag ctatgagaaa gcgccacgct tcccgaaggg agaaaggcgg acaggtatcc     6360
ggtaagcggc agggtcggaa caggagagcg cacgagggag cttccagggg gaaacgcctg     6420
gtatctttat agtcctgtcg ggtttcgcca cctctgactt gagcgtcgat ttttgtgatg      6480
ctcgtcaggg gggcggagcc tatggaaaaa cgccagcaac gcggcctttt tacggttcct     6540
ggccttttgc tggccttttg ctcacatgtt ctttcctgcg ttatccctg attctgtgga       6600 taaccgtatt accgc                                                      6615
```

```
<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Arg Arg Arg Arg Arg Arg Arg Arg
1               5
```

CHLOROALKANE PENETRATION METHOD FOR QUANTIFYING ACCESS OF A MOLECULE INTO A CELL

CROSS-REFERENCE TO RELATED APPLICATIONS

This application claims the benefit of and priority to U.S. Provisional Patent Application Ser. No. 62/424,955 filed Nov. 21, 2016, which is incorporated herein by reference in its entirety.

STATEMENT OF RIGHTS TO INVENTIONS MADE UNDER FEDERALLY SPONSORED RESEARCH

This invention was made with government support under grant number AI109725 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 15, 2018, is named 167774_011501US_SL.txt and is 21,027 bytes in size.

BACKGROUND OF THE INVENTION

Determining the quantity and location of a molecule in a cell with a high degree of accuracy is a technically challenging process. The most common methods used to quantify cellular penetration of an exogenously added molecule include monitoring the uptake of dye-labeled molecules by microscopy or flow cytometry. Alternatively, cell penetration assays can include transcriptional readouts, quantitative mass spectrometry readouts, or dye-mediated methods that produce signals based on changing chemical environment.

These methods can be technically challenging, lack the spatial acuity to distinguish molecules that are trapped in endosomes from material in the cytosol, and are prone to additional artifacts, such as leakage of a fluorescent molecule during physical manipulation or after fixation and light-induced redistribution of signal from a fluorescent molecule. Furthermore, existing methods to quantify penetration of a molecule often require the molecule of interest to be conjugated to a bulky chemical group that perturbs the molecule's physical properties and molecular interactions, and/or require expensive instruments, such as microscopes for imaging. In nearly all cases, these methods cannot provide a highly quantitative measurement.

Accordingly, improved methods for identifying and quantifying molecules in cellular compartments are needed.

SUMMARY OF THE INVENTION

As described below, the invention provides methods for localizing and quantifying the extent to which a molecule penetrates a cell.

In one aspect, the invention features a method for quantifying cell penetration of an agent, the method involving contacting a cell with an agent conjugated to chloroalkane, wherein the cell expresses chloroalkane dehalogenase; contacting the cell with chloroalkane conjugated to a detectable moiety; and detecting a signal from the detectable moiety, wherein the signal indicates the cell penetration of the molecule of interest conjugated to chloroalkane.

In another aspect, the invention features a method for quantifying cell penetration of an agent of interest, the method involving contacting a cell with an agent conjugated to chloroalkane, wherein the cell expresses a fusion protein comprising chloroalkane dehalogenase fused to a detectable reporter; contacting the cell with chloroalkane conjugated to a detectable moiety; and detecting a signal from the detectable moiety, wherein the level of the signal indicates the cell penetration of the molecule of interest conjugated to chloroalkane. In one embodiment, the signal from the detectable moiety is inversely proportional to the signal associated with binding of chloroalkane dehalogenase to the agent conjugated to chloroalkane. In another embodiment, the chloroalkane dehalogenase is fused to a protein that localizes the chloroalkane dehalogenase to a cellular compartment. In another embodiment, the cellular compartment is cytosol, a cellular organelle or other membrane-bound compartment selected from the group consisting of endosome, endoplasmic reticulum, Golgi apparatus, lysosomes, microtubules, mitochondria, mitochondrial intermembrane space, nucleus, peroxisomes, perinuclear recycling compartment, and ribosomes.

In another aspect, the invention features a method for quantifying cell penetration of an agent of interest, the method involving contacting a cell with the agent conjugated to chloroalkane, wherein the cell expresses chloroalkane dehalogenase; and detecting a covalent conjugate between the agent and chloroalkane dehalogenase.

In another aspect, the invention features a cell (e.g., eukaryotic or prokaryotic cell) expressing a fusion protein comprising chloroalkane dehalogenase fused to a detectable reporter that localizes the fusion protein to the nucleus, mitochondria, cytoplasm, give small molecule known cell penetrant fused to chloroalkane, give amount of chloroalkane tag that could be added to your molecule of interest.

In another aspect, the invention features a method of conjugating an agent of interest with chloroalkane, the method involving covalently linking an agent of interest comprising a free amine group and chloroalkane ligand. In one embodiment, the conjugating is carried out in the presence of a coupling agent (e.g., benzotriazol-1-yl-oxytripyrrolidino-phosphonium hexafluorophosphate (PyBOP)).

In another aspect, the invention features a kit for characterizing cell penetration of an agent, the kit comprising a cell expressing a fusion protein comprising chloroalkane dehalogenase fused to a detectable reporter.

In another aspect, the invention features a kit for linking an agent of interest to a chloroalkane ligand, the kit comprising the chloroalkane ligand and a coupling reagent. In one embodiment, the coupling reagent is benzotriazol-1-yl-oxytripyrrolidino-phosphonium hexafluorophosphate (PyBOP). In another embodiment, the kit further comprises N,N-Diisopropylethylamine (DIPEA).

In another aspect, the invention features a kit for characterizing cell penetration of an agent, the kit comprising a cell expressing a fusion protein containing chloroalkane dehalogenase fused to a detectable reporter, a chloroalkane ligand, and a coupling reagent.

In various embodiments of any of the above aspects, the agent is a bacterium, nucleic acid molecule, polypeptide (or fragment thereof), small molecule, viral particle, nanoparticle, and macromolecule (e.g., a synthetic macromolecule, polymer, or dendrimer). In various embodiments of any of the above aspects, the detectable moiety is a cell permeable fluorescent tag. In various embodiments of any of the above aspects, the fluorescent tag is HaloTag Coumarin, HaloTag diAcFAM, HaloTag Oregon Green, tetramethyl rhodamine (TMR), and tetrazine-tetramethylrhodamine (TAMRA). In various embodiments of any of the above aspects, the signal is detected by fluorescence spectroscopy, flow cytometry, or mass spectrometry. In various embodiments of any of the above aspects, the signal from the detectable moiety co-localizes with the signal from the detectable reporter. In various embodiments of any of the above aspects, the eukaryotic cell is a mammalian cell, stem cell, primary human cell, or protozoa and the prokaryotic cell is a yeast cell or bacteria cell.

Definitions

Unless defined otherwise, all technical and scientific terms used herein have the meaning commonly understood by a person of ordinary skill in the art to which this invention belongs. The following references provide one of ordinary skill in the art with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, macromolecular chemical compound, antibody, nucleic acid molecule, nanoparticle, viral particle, cell or bacterium, or polypeptide, or fragments thereof.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include unnatural portions, such as incorporation of unnatural amino acids into a polypeptide.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" or "detectable moiety" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, fluorescent molecules, electron-dense reagents, enzymes (for example, as commonly used in an ELISA), biotin, digoxigenin, haptens, or specifically reactive chemical groups. In some embodiments, the detectable moeity is a detectable protein. In some embodiments, the detectable protein is a fluorescent protein (e.g., enhanced green fluorescent protein (eGFP)) or a fluorescent molecule.

By "Haloenzyme" or "Haloenzyme polypeptide" is meant a protein having at least about 85% amino acid identity to the sequence the provided by PROMEGA. An exemplary Haloenzyme amino acid sequence is provided below (SEQ ID NO: 1):

```
MAEIGTGFPF DPHYVEVLGE RMHYVDVGPR DGTPVLFLHG NPTSSYVWRN IIPHVAPTHR    60

CIAPDLIGMG KSDKPDLGYF FDDHVRFMDA FIEALGLEEV VLVIHDWGSA LGFHWAKRNP   120

ERVKGIAFME FIRPIPTWDE WPEFARETFQ AFRTTDVGRK LIIDQNVFIE GTLPMGVVRP   180

LTEVEMDHYR EPFLNPVDRE PLWRFPNELP IAGEPANIVA LVEEYMDWLH QSPVPKLLFW   240

GTPGVLIPPA EAARLAKSLP NCKAVDIGPG LNLLQEDNPD LIGSEIARWL STLEISG      297
```

By "Haloenzyme polynucleotide" is meant a nucleic acid molecule encoding a Haloenzyme polypeptide. An exemplary Haloenzyme polynucleotide sequence is provided below (SEQ ID NO: 2):

```
atggcagaaa tcggtactgg ctttccattc gaccccatt  atgtggaagt cctgggcgag    60
cgcatgcact acgtcgatgt tggtccgcgc gatggcaccc ctgtgctgtt cctgcacggt   120
aacccgacct cctcctacgt gtggcgcaac atcatcccgc atgttgcacc gacccatcgc   180
tgcattgctc cagacctgat cggtatgggc aaatccgaca aaccagacct gggttatttc   240
ttcgacgacc acgtccgctt catggatgcc ttcatcgaag ccctgggtct ggaagaggtc   300
gtcctggtca ttcacgactg gggctccgct ctgggtttcc actgggccaa gcgcaatcca   360
gagcgcgtca aaggtattgc atttatggag ttcatccgcc ctatcccgac ctgggacgaa   420
tggccagaat ttgcccgcga gaccttccag gccttccgca ccaccgacgt cggccgcaag   480
```

-continued

```
ctgatcatcg atcagaacgt ttttatcgag ggtacgctgc cgatgggtgt cgtccgcccg  540
ctgactgaag tcgagatgga ccattaccgc gagccgttcc tgaatcctgt tgaccgcgag  600
ccactgtggc gcttcccaaa cgagctgcca atcgccggtg agccagcgaa catcgtcgcg  660
ctggtcgaag aatacatgga ctggctgcac cagtcccctg tcccgaagct gctgttctgg  720
ggcaccccag gcgttctgat cccaccggcc gaagccgctc gcctggccaa aagcctgcct  780
aactgcaagg ctgtggacat cggcccgggt ctgaatctgc tgcaagaaga caacccggac  840
ctgatcggca gcgagatcgc gcgctggctg tcgacgctcg agatttccgg c            891
```

By "Halo-GFP-mitochondrial fission factor (Mff) polypeptide" or "Halo-GFP-mitochondrial fission factor (Mff) protein" is meant a protein having at least about 85% amino acid identity to the sequence as described by Friedman et al. (Science. 2011. Oct. 21; 334(6054): pp. 358-62). An exemplary Haloenzyme amino acid sequence is provided below (SEQ ID NO: 3):

```
MAEIGTGFPF DPHYVEVLGE RMHYVDVGPR DGTPVLFLHG NPTSSYVWRN IIPHVAPTHR   60

CIAPDLIGMG KSDKPDLGYF FDDHVRFMDA FIEALGLEEV VLVIHDWGSA LGFHWAKRNP  120

ERVKGIAFME FIRPIPTWDE WPEFARETFQ AFRTTDVGRK LIIDQNVFIE GTLPMGVVRP  180

LTEVEMDHYR EPFLNPVDRE PLWRFPNELP IAGEPANIVA LVEEYMDWLH QSPVPKLLFW  240

GTPGVLIPPA EAARLAKSLP NCKAVDIGPG LNLLQEDNPD LIGSEIARWL STLEISGYTM  300

VSKGAELFTG IVPILIELNG DVNGHKFSVS GEGEGDATYG KLILKFICIT GKLPVPWPTL  360

VTTLSYGVQC FSRYPDHMKQ HDFFKSAMPE GYIQERTIFF EDDGNYKSRA EVKFEGDTLV  420

NRIELIGTDF KEDGNILGNK MEYNYNAHNV YIMTDKAKNG IKVNFKIRHN IEDGSVQLAD  480

HYQQNTPIGD GPVLLPDNHY LSTQSALSKD PNEKRDHMIY FGFVTAAAIT HGMDELYKSG  540

LRSRVMSKGT SSDTSLGRVS RAAFPSPTAA EMAEISRIQY EMEYTEGISQ RMRVPEKLKV  600

APPNADLEQG FQEGVPNASV IMQVPERIVV AGNNEDVSFS RPADLDLIQS TPFKPLALKT  660

PPRVLTLSER PLDFLDLERP PTTPQNEEIR AVGRLKRERS MSENAVRQNG QLVRNDSLWH  720

RSDSAPRNKI SRFQAPISAP EYTVTPSPQQ ARVCPPHMLP EDGANLSSAR GILSLIQSST  780

RRAYQQILDV LDENRRPVLR GGSAAATSNP HHDNVRYGIS NIDTTIEGTS DDLTVVDAAS  840

LRRQIIKLNR RLQLLEEENK ERAKREMVMY SITVAFWLLN SWLWFRR               887
```

By "Halo-GFP-mitochondrial fission factor (Mff) polynucleotide" is meant a nucleic acid molecule encoding a Halo-GFP-Mff polypeptide. The Halo-GFP-Mff polypeptide can be produced by, for example, Addgene (plasmid #49153). An exemplary Halo-GFP-Mff polynucleotide sequence is provided below (SEQ ID NO: 4):

```
catgcattag ttattaatag taatcaatta cggggtcatt agttcatagc ccatatatgg   60
agttccgcgt tacataactt acggtaaatg gcccgcctgg ctgaccgccc aacgaccccc  120
gcccattgac gtcaataatg acgtatgttc ccatagtaac gccaataggg actttccatt  180
gacgtcaatg ggtggagtat ttacggtaaa ctgcccactt ggcagtacat caagtgtatc  240
atatgccaag tacgcccect attgacgtca atgacggtaa atggcccgcc tggcattatg  300
cccagtacat gaccttatgg gactttccta cttggcagta catctacgta ttagtcatcg  360
ctattaccat ggtgatgcgg ttttggcagt acatcaatgg gcgtggatag cggtttgact  420
cacggggatt tccaagtctc cacccattg acgtcaatgg gagtttgttt tggcaccaaa  480
```

-continued

```
atcaacggga ctttccaaaa tgtcgtaaca actccgcccc attgacgcaa atgggcggta    540
ggcgtgtacg gtgggaggtc tatataagca gagctggttt agtgaaccgt cagatccgct    600
agcgctaccg gtcgccatgg cagaaatcgg tactggcttt ccattcgacc cccattatgt    660
ggaagtcctg ggcgagcgca tgcactacgt cgatgttggt ccgcgcgatg cacccctgt     720 gctgttcctg cacggtaacc cgacctcctc ctacgtgtgg cgcaacatca tcccgcatgt    780
tgcaccgacc catcgctgca ttgctccaga cctgatcggt atgggcaaat ccgacaaacc    840
agacctgggt tatttcttcg acgaccacgt ccgcttcatg gatgccttca tcgaagccct    900
gggtctggaa gaggtcgtcc tggtcattca cgactgggc tccgctctgg gtttccactg     960
ggccaagcgc aatccagagc gcgtcaaagg tattgcattt atggagttca tccgccctat   1020
cccgacctgg gacgaatggc cagaatttgc ccgcgagacc ttccaggcct tccgcaccac   1080
cgacgtcggc cgcaagctga tcatcgatca gaacgttttt atcgagggta cgctgccgat   1140
gggtgtcgtc cgcccgctga ctgaagtcga gatggaccat taccgcgagc cgttcctgaa   1200
tcctgttgac cgcgagccac tgtggcgctt cccaaacgag ctgccaatcg ccggtgagcc   1260
agcgaacatc gtcgcgctgg tcgaagaata catggactgg ctgcaccagt cccctgtccc   1320
gaagctgctg ttctggggca ccccaggcgt tctgatccca ccggccgaag ccgctcgcct   1380
ggccaaaagc ctgcctaact gcaaggctgt ggacatcggc ccgggtctga atctgctgca   1440
agaagacaac ccggacctga tcggcagcga gatcgcgcgc tggctgtcga cgctcgagat   1500
ttccggttac accatggtga gcaagggcgc cgagctgttc accggcatcg tgcccatcct   1560
gatcgagctg aatggcgatg tgaatggcca caagttcagc gtgagcggcg agggcgaggg   1620
cgatgccacc tacggcaagc tgaccctgaa gttcatctgc accaccggca agctgcctgt   1680
gccctggccc accctggtga ccaccctgag ctacggcgtg cagtgcttct cacgctaccc   1740
cgatcacatg aagcagcacg acttcttcaa gagcgccatg cctgagggct acatccagga   1800
gcgcaccatc ttcttcgagg atgacggcaa ctacaagtcg cgcgccgagg tgaagttcga   1860
gggcgatacc ctggtgaatc gcatcgagct gaccggcacc gatttcaagg aggatggcaa   1920
catcctgggc aataagatgg agtacaacta caacgcccac aatgtgtaca tcatgaccga   1980
caaggccaag aatggcatca aggtgaactt caagatccgc cacaacatcg aggatggcag   2040
cgtgcagctg gccgaccact accagcagaa taccccatc ggcgatggcc ctgtgctgct   2100
gcccgataac cactacctgt ccacccagag cgccctgtcc aaggacccca cgagaagcg    2160 cgatcacatg atctacttcg gcttcgtgac cgccgccgcc atcacccacg gcatggatga   2220
gctgtacaag tccggactca gatctcgagt gatgagtaaa ggaacaagca gtgacacatc   2280
actaggaagg gtgagcaggg cagcatttcc ttctcccact gctgctgaga tggcagaaat   2340
tagtcgaatt cagtacgaaa tggaatatac tgaaggcatt agtcagcgaa tgagggtccc   2400
agaaaagtta aaagtagcac cgccaaacgc tgacctggaa caaggattcc aagaaggagt   2460
tccaaatgct agtgtgataa tgcaagttcc ggagaggatt gttgtagcag gaaataatga   2520
agatgtttca ttttcaagac cagcagatct tgaccttatt cagtcaactc cctttaaacc   2580
cctggcactg aaaacaccac ctcgtgtact tacgctgagt gaaagaccac tagattttct   2640
ggatttagaa agacctccta caaccccctca aaatgaagaa atccgagcag ttggcagact   2700
aaaaagagag cggtctatga gtgaaaatgc tgttcgccaa aatggacagc tggtcagaaa   2760
tgattctctg tggcacagat cagattctgc cccaagaaat aaaatttcaa ggttccaggc   2820
accgatttct gcaccggagt acactgtgac accatcgcca caacaggctc gggtctgtcc   2880
```

```
tccccatatg ttacctgaag atggagctaa tctttcctct gctcgtggca ttttgtcgct    2940
tatccagtct tctactcgta gggcatacca gcagatcttg gatgtgctgg atgaaaatcg    3000
cagacctgtg ttgcgtggtg ggtctgctgc cgccacttct aatcctcatc atgacaacgt    3060
caggtatggc atttcaaata tagatacaac cattgaagga acgtcagatg acctgactgt    3120
tgtagatgca gcttcactaa gacgacagat aatcaaacta aatagacgtc tacaacttct    3180
ggaagaggag aacaaagaac gtgctaaaag agaaatggtc atgtattcaa ttactgtagc    3240
tttctggctg cttaatagct ggctctggtt tcgccgctag ggatccaccg gatctagata    3300
actgatcata atcagccata ccacatttgt agaggtttta cttgctttaa aaacctccc    3360 acacctcccc ctgaacctga aacataaaat gaatgcaatt gttgttgtta acttgtttat    3420
tgcagcttat aatggttaca aataaagcaa tagcatcaca aatttcacaa ataaagcatt    3480
tttttcactg cattctagtt gtggtttgtc caaactcatc aatgtatctt aacgcgtaaa    3540
ttgtaagcgt taatattttg ttaaaattcg cgttaaattt ttgttaaatc agctcatttt    3600
ttaaccaata ggccgaaatc ggcaaaatcc cttataaatc aaaagaatag accgagatag    3660
ggttgagtgt tgttccagtt tggaacaaga gtccactatt aaagaacgtg gactccaacg    3720
tcaaagggcg aaaaaccgtc tatcagggcg atggcccact acgtgaacca tcaccctaat    3780
caagtttttt ggggtcgagg tgccgtaaag cactaaatcg aaccctaaa gggagccccc    3840 gatttagagc ttgacgggga aagccggcga acgtggcgag aaaggaaggg aagaaagcga    3900
aaggagcggg cgctagggcg ctggcaagtg tagcggtcac gctgcgcgta accaccacac    3960
ccgccgcgct taatgcgccg ctacaggcgc cgtcaggtgg cacttttcgg ggaaatgtgc    4020
gcggaacccc tatttgttta tttttctaaa tacattcaaa tatgtatccg ctcatgagac    4080
aataaccctg ataaatgctt caataatatt gaaaaaggaa gagtcctgag gcggaaagaa    4140
ccagctgtgg aatgtgtgtc agttagggtg tggaaagtcc ccaggctccc cagcaggcag    4200
aagtatgcaa agcatgcatc tcaattagtc agcaaccagg tgtggaaagt ccccaggctc    4260
cccagcaggc agaagtatgc aaagcatgca tctcaattag tcagcaacca tagtcccgcc    4320
cctaactccg cccatcccgc ccctaactcc gcccagttcc gcccattctc cgccccatgg    4380
ctgactaatt ttttttattt atgcagaggc cgaggccgcc tcggcctctg agctattcca    4440
gaagtagtga ggaggctttt ttggaggcct aggcttttgc aaagatcgat caagagacag    4500
gatgaggatc gtttcgcatg attgaacaag atggattgca cgcaggttct ccggccgctt    4560
gggtggagag gctattcggc tatgactggg cacaacagac aatcggctgc tctgatgccg    4620
ccgtgttccg gctgtcagcg caggggcgcc cggttctttt tgtcaagacc gacctgtccg    4680
gtgccctgaa tgaactgcaa gacgaggcag cgcggctatc gtggctggcc acgacgggcg    4740
ttccttgcgc agctgtgctc gacgttgtca ctgaagcggg aagggactgg ctgctattgg    4800
gcgaagtgcc ggggcaggat ctcctgtcat ctcaccttgc tcctgccgag aaagtatcca    4860
tcatggctga tgcaatgcgg cggctgcata cgcttgatcc ggctacctgc ccattcgacc    4920
accaagcgaa acatcgcatc gagcgagcac gtactcggat ggaagccggt cttgtcgatc    4980
aggatgatct ggacgaagag catcaggggc tcgcgccagc cgaactgttc gccaggctca    5040
aggcgagcat gcccgacggc gaggatctcg tcgtgaccca tggcgatgcc tgcttgccga    5100
atatcatggt ggaaaatggc cgcttttctg gattcatcga ctgtggccgg ctgggtgtgg    5160
cggaccgcta tcaggacata gcgttggcta cccgtgatat tgctgaagag cttggcggcg    5220
aatgggctga ccgcttcctc gtgctttacg gtatcgccgc tcccgattcg cagcgcatcg    5280
ccttctatcg ccttcttgac gagttcttct gagcgggact ctggggttcg aaatgaccga    5340
```

-continued

```
ccaagcgacg cccaacctgc catcacgaga tttcgattcc accgccgcct tctatgaaag 5400
gttgggcttc ggaatcgttt tccgggacgc cggctggatg atcctccagc gcggggatct 5460
catgctggag ttcttcgccc accctagggg gaggctaact gaaacacgga aggagacaat 5520
accggaagga acccgcgcta tgacggcaat aaaaagacag aataaaacgc acggtgttgg 5580
gtcgtttgtt cataaacgcg gggttcggtc ccagggctgg cactctgtcg atacccacc 5640 gagacccat tggggccaat acgcccgcgt ttcttccttt tccccacccc accccccaag 5700
ttcgggtgaa ggcccagggc tgcagccaa cgtcggggcg gcaggccctg ccatagcctc 5760
aggttactca tatatacttt agattgattt aaaacttcat ttttaattta aaaggatcta 5820
ggtgaagatc cttttgata atctcatgac caaaatccct taacgtgagt tttcgttcca 5880
ctgagcgtca gacccgtag aaaagatcaa aggatcttct tgagatcctt tttttctgcg 5940
cgtaatctgc tgcttgcaaa caaaaaaacc accgctacca gcggtggttt gtttgccgga 6000
tcaagagcta ccaactcttt ttccgaaggt aactggcttc agcagagcgc agataccaaa 6060
tactgttctt ctagtgtagc cgtagttagg ccaccacttc aagaactctg tagcaccgcc 6120
tacatacctc gctctgctaa tcctgttacc agtggctgct gccagtggcg ataagtcgtg 6180
tcttaccggg ttggactcaa gacgatagtt accggataag gcgcagcggt cgggctgaac 6240 gggggggttcg tgcacacagc ccagcttgga gcgaacgacc tacaccgaac tgagatacct 6300
acagcgtgag ctatgagaaa gcgccacgct tcccgaaggg agaaaggcgg acaggtatcc 6360
ggtaagcggc agggtcggaa caggagagcg cacgagggag cttccagggg gaaacgcctg 6420
gtatctttat agtcctgtcg ggtttcgcca cctctgactt gagcgtcgat ttttgtgatg 6480
ctcgtcaggg gggcggagcc tatggaaaaa cgccagcaac gcggccttt tacggttcct 6540 ggccttttgc tggccttttg ctcacatgtt ctttcctgcg ttatccctg attctgtgga 6600 taaccgtatt accgc                                                   6615
```

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

The terms "protein," "polypeptide," and "peptide" are used interchangeably herein to include any molecule comprising a plurality of amino acid residues linked by peptide or amide bonds.

As used herein, "obtaining" as in "obtaining an agent" includes synthesizing, purchasing, or otherwise acquiring the agent.

By "reduces" is meant a negative alteration of at least 10%, 25%, 50%, 75%, or 100%.

By "reference" is meant a standard or control condition.

A "vector" or "expression vector" is a composition of matter that comprises an isolated polynucleotide and that may be used to deliver the isolated polynucleotide to the interior of a cell. Numerous vectors are known in the art including, but not limited to, linear polynucleotides, polynucleotides associated with ionic or amphiphilic compounds, plasmids, and viruses. Thus, the term "vector" or "expression vector" includes an autonomously replicating plasmid or a virus. The term should also be construed to include non-plasmid and non-viral compounds that facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression may be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide. In some embodiments, the expression vector is a plasmid (e.g., high expression plasmid). In particular embodiments, the host cell is a bacterium (e.g., *Escherichia coli* (*E. coli*)).

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A provides a schematic showing the experimental procedure of CAPA, which uses a HaloEnzyme-GFP-expressing HeLa cell line. Untreated cells labeled with Halo-ligand (HaloTag, HTag) conjugated to tetrazine-tetramethylrhodamine (TAMRA) showed a large increase in red fluorescence as measured by flow cytometry. For CAPA, cells are pre-treated with vehicle or peptide, washed, and chased with HTag-TAMRA. Cells treated with cell-penetrant molecules have had their HaloEnzyme blocked, thus preventing the HTag-TAMRA from covalently labeling the cells. In this schematic, the molecule of interest is a peptide.

FIG. 1B provides a panel of representative images showing cells after CAPA, showing HaloEnzyme-GFP fluorescence, HTag-TAMRA fluorescence and the overlay of the two. A representative image of cells treated with HTag-cTMP at 2.5 µM shows roughly 90% inhibition of the HTag-TAMRA signal. A representative image of cells treated with HTag-DD5-o at 10 µM shows roughly 50% inhibition of signal.

FIG. 1C provides a graph showing the dose-dependent response curve of HTag-TAMRA signal after pre-incubation with different concentrations of HTag-cTMP, HTag-DD5o, and the negatively charged, linear variant HTag-DD5-neg. Data was normalized using the values obtained for vehicle (0% HTag-TAMRA signal inhibition) and for vehicle with no HTag-TAMRA added (100% signal inhibition). Points are means from three independent experiments and error bars show standard deviation.

FIG. 1D provides images showing the chemical structures of HTag-cTMP, HTag-DD5o, and HTag-DD5-neg compounds.

FIG. 2A provides a scatter plot showing each measurement, which involved 10,000 cells, gated as shown to count only live cells. This is the standard gating procedure for flow cytometry assays on HeLa cells.

FIG. 2B provides a graph showing flow cytometry data from CAPA, where HTag-DD5neg shows little inhibition of HTag-TAMRA fluorescence, even at concentrations approaching its solubility limit.

FIG. 2C provides a graph showing flow cytometry data from CAPA, where the small molecule HTag-cTMP shows dose-dependent inhibition of HTag-TAMRA fluorescence.

FIG. 2D provides a graph showing flow cytometry data from CAPA, where HTag-DD5-o shows a similar trend as HTag-cTMP, but at roughly 100-fold higher concentration. This ratio is to be expected when comparing a cell-penetrant small molecule to a peptide.

As shown in FIGS. 2A-2D, for each independent trial, mean fluorescence intensity values were calculated. These data were then normalized to the no-TAMRA signal (DMSO, shown in gray) as the 0% value, and the no-peptide signal (DMSO+TAMRA, shown in bright green) as the 100% value.

FIG. 5A shows time courses for cytosolic penetration of Trp and DD5-o. FIG. 5B shows the effect of serum on cytosolic penetration of DD5-o (4 hr incubation at 37° C.). Values are $CP_{50}$ with standard deviation (std. dev.) from 3 independent trials. FIG. 5C shows the cytosolic penetration of biomolecules (DD5-o, $Arg_9$ (SEQ ID NO: 5), AntP, and Tat) after 4 hour incubation at 4° C. or 37° C. These data were obtained in duplicate. For each concentration in FIG. 5C, the left bar on the graph shows the cytosolic penetration of benchmark molecules after 4 hour (hr) incubation at 37° C., and the right bar on the graph shows the cytosolic penetration of benchmark molecules after 4 hour incubation at 4° C. FIG. 5D shows the effect of endocytosis inhibitors (chlorpromazine, dynasore, and EIPA (ethyl isopropyl amiloride)) on cytosolic penetration. 50 µM of the indicated endocytosis inhibitor was added to cells for 1 hr, then the indicated biomolecules were added and incubated for 4 hr at 37° C. Error bars denote std. dev. from 3 independent trials. For each concentration in FIG. 5D, the bar on the far left is "none," the bar that is second from the far left and next to "none" is "cholorpromazine," the bar that is third from the far left and next to "cholorpromazine" is "dynasore," and the bar on the far right of each concentration is EIPA.

FIG. 6A are representative images showing HeLa cells with stably-expressed HaloTag-GFP-H2B fusion proteins, which localizes to the nucleus (top left image). HeLa cells with stably-expressed HaloTag-GFP-H2B fusion proteins and treated with cTMP are shown in the top right image of FIG. 6A. HeLa cells with stably-expressed HaloTag-GFP-H2B fusion proteins and treated with a chloroalkane-dye are shown in the bottom left image of FIG. 6A. HeLa cells with stably-expressed HaloTag-GFP-H2B fusion proteins and treated with cTMP and a chloroalkane-dye are shown in the bottom right image of FIG. 6A. FIG. 6B is a graph showing CAPA data for nuclear penetration of the small molecule Trp, lipid nanoparticle LNP-1, and peptides DD5-o and LL5-o (Table 1). FIG. 6C is a schematic and graphs illustrating how penetration profiling related to endosomal, cytosolic, and nuclear localization would be carried out.

FIG. 7A is a schematic and graph illustrating how mechanistic profiles from FIG. 6C could be obtained for labeled LNPs and LNPs with labeled cargoes. FIG. 7B is a graph showing dose dependency of cytosolic penetration for LNPs. LNPs were prepared with 16 equivalents (equiv.) bioreducible lipid, 4 equiv. cholesterol, 1 equiv. DOPE (1,2-Dioleoyl-sn-glycero-3-phosphoethanolamine), and 1, 2, 3, or 4 equiv. chloroalkane-DSPE (LNP-1, LNP-2, LNP-3, and LNP-4, respectively; DSPE is 1,2-Distearoyl-sn-glycero-3-phosphoethanolamine).

DETAILED DESCRIPTION OF THE INVENTION

Figure 1A:
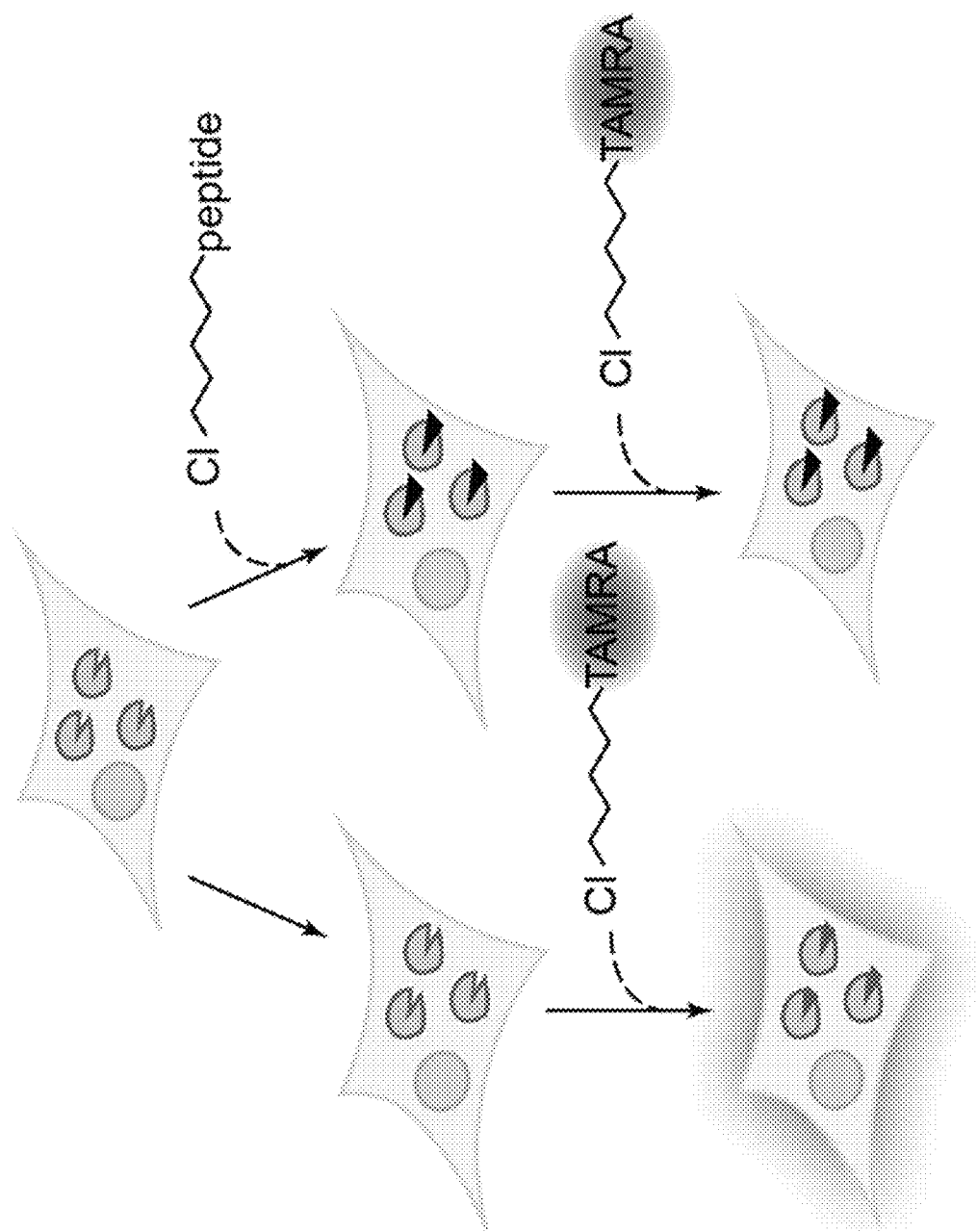
FIGS. 1A-1D show data obtained by the Chloroalkane Penetration Assay (CAPA), which quantified the relative cytosolic access of exogenously added DD5-o.

The invention provides methods for quantifying the extent to which a molecule penetrates a cell.

The invention is based, at least in part, on the discovery of an assay, referred to herein as "Chloroalkane Penetration Assay" (CAPA) for measuring cell penetration of an exogenously applied molecule. This assay was used to quantitate the cell penetration of DD5-o, which is a stapled peptide that induces autophagy. CAPA uses a cell line that stably expresses a cytosolically-oriented protein as a fusion with green fluorescent protein (GFP) and a modified bacterial chloroalkane dehalogenase (referred to herein as "Haloenzyme") that covalently labels itself with a small, otherwise inert small chloroalkane (referred to herein as "Haloligand" or "Htag"). If an exogenously added molecule bearing the Haloligand reaches the cytosol, it reacts exclusively with the HaloEnzyme and blocks its active site. Following this incubation period, the amount of unreacted HaloEnzyme was measured by chasing with a Haloligand-bearing dye (here, Htag-TAMRA). The relative amount of red cellular fluorescence after this chase was then quantified by flow cytometry. The red signal reported directly on the amount of free Haloenzyme, which was inversely proportional to the degree to which the added molecule accessed the cytoplasm during the incubation period. Thus, the rapid, inexpensive CAPA method confirmed the cytosolic localization of HTag-DD5-o at micromolar concentrations, which correlates with the concentrations at which the DD5-o activates autophagy.

HaloTag Labeling System

The invention employs the HaloTag enzyme labeling system to measure cell penetration. The HaloTag system provides a HaloEnzyme, which is a modified bacterial chloroalkane dehalogenase that covalently labels itself with the small, otherwise inert Haloligand functional group. The Haloenzyme can be genetically expressed in cells using conventional expression vectors. Commercially available expression vectors typically contain an enhancer or promoter (e.g., CMV) for strong, constitutive or inducible expression in many cell types. The HaloEnzyme is a 33 kDa monomeric protein that can be used to generate N- or C-terminal fusions using conventional genetic means, such as fusion to fluorescent proteins to verify faithful and robust expression, or fusion to a protein or sequence that specifically localizes the fusion construct to a specific cell compartment, or fusion to any protein of interest. Haloenzyme fusion proteins can be efficiently expressed in a variety of cell types, and expression could be controlled by inducible promoters for specific applications. The HaloEnzyme can be oriented exclusively in various cellular compartments (e.g., the cytosol) using conventional genetic means. The HaloEnzyme is a monomeric protein not endogenous to mammalian, plant or *E. coli* cells; therefore, levels of nonspecific activity are minimized, while a high degree of labeling specificity is achieved.

The HaloEnzyme generated by the expression vector is a mutant haloalkane dehalogenase, which forms a covalent bond with the Haloligand, which consists of a selectively reactive chloroalkane linker. Under physiological conditions this covalent bond forms rapidly and is highly specific and irreversible, yielding a complex that is stable even under harsh conditions. The HaloTag technology, which collectively encompasses the expression of HaloEnzyme or a HaloEnzyme-containing protein construct plus the application of a Haloligand-containing molecule (typically, but not exclusively, a small molecule or dye), can be successfully applied in many systems, including: bacteria, mammalian cells, plants, and yeast. Examples of systems in which HaloTag technology can be applied are described by Kosaka et al. (Bioconjugate Chem. 2009. 20, 1367-74), Lee et al. (J. Am. Chem. Soc. 2010. 132, 15099-101), Huybrechts et al.

(Traffic. 2009. 10, 1722-33), Lang et al. (J. Exp. Bot. 2006. 57, 2985-92), and Reek-Peterson et al. (Proc. Natl. Acad. Sci. 2009. 106, 5669-74), which are incorporated herein by reference in their entirety.

The HaloTag system provides a customizable Haloenzyme expression vector. Restriction sites are available for creating a C- or N-terminal fusion protein, and conventional cloning means allows application of Haloenzyme within any expression vector. Thus, the provided elements in the expression vector allow for the expression of fusion proteins in many cell types. An expression vector encoding the HaloEnzyme or fusion protein can be introduced into mammalian cells by either transient transfection or generation of stable cell lines expressing the HaloEnzyme. At some point in the process, a Haloligand-containing molecule is introduced to the cells, where it readily crosses the cell membrane and covalently binds to the HaloEnzyme. The kinetics of this interaction is rapid, requiring only 5-60 minutes of incubation. The unbound ligand is typically washed out, and the user can then continue with the desired application, for example, fluorescence imaging of live or fixed cells. Furthermore, the interchangeability of the ligands facilitates imaging at different wavelengths or incorporating novel functionalities without changing the underlying genetic construct.

Cell Types

The CAPA method can be applied to any prokaryotic or eukaryotic cell type, for example, cells that are commonly utilized in molecular biology applications. Commonly used prokaryotic cell types can include, for example, *Aliivibrio fischeri, Bacillus subtilis, Burkholderia mallei, Caulobacter crescentus, Escherichia coli, Lactobacillus acidophilus, Mycoplasma genitalium, Pseudomonas fluorescens, Streptococcus pneumonia* and *Yersinia pestis*. Commonly used eukaryotic cell types can include, for example DU145 (prostate cancer), H295R (adrenocortical cancer), HeLa (cervical cancer), KBM-7 (chronic myelogenous leukemia), LNCaP (prostate cancer), MCF-7 (breast cancer), MDA-MB-468 (breast cancer), PC3 (prostate cancer), SaOS-2 (bone cancer), SH-SY5Y (neuroblastoma,), T47D (breast cancer), THP-1 (acute myeloid leukemia), U87 (glioblastoma), National Cancer Institute's 60 cancer cell line panel (NCI60), Vero (African green monkey Chlorocebus kidney epithelial cell line), MC3T3 (embryonic calvarium), GH3 (pituitary tumor), PC12 (pheochromocytoma), MDCK (kidney epithelial), AB9 (zebrafish), *Chlamydomonas reinhardtii* (green algae), *Schizosaccharomyces pombe* (yeast), *Saccharomyces cerevisiae* (yeast) and *Arabidopsis thaliana* (plant), and BY-2 (tobacco) cells. Examples of eukaryotic cells known to be used in molecular biology applications include, 3T3-L1, 4T1, 9L, A172, A20, A253, A2780, A2780ADR, A2780cis, A431, A549, AHL-1, ALC, B16, B35, BCP-1, BEAS-2B, bEnd.3, BHK-21, BOSC23, BT-20, BxPC3, C2C12, C3H-10T1/2, C6, C6/36, Caco-2, Cal-27, CGR8, CHO, CML T1, CMT12, COR-L23, COR-L23/5010, COR-L23/CPR, COR-L23/R23, COS-7, COV-434, CT26, D17, DH82, DuCaP, E14Tg2a, EL4, EM-2, EM-3, EMT6/AR1, EMT6/AR10.0, FM3, GL261, H1299, HaCaT, HCA2, HEK 293, HEK 293T, Hepa1c1c7, Hep G2, High Five, HL-60, HT-1080, HT-29, J558L, Jurkat, JY, K562, KCL-22, KG1, Ku812, KYO-1, L1210, L243, MA2.1Ma-Mel 1, 2, 3-48, MC-38, MCF-10A, MDA-MB-157, MDA-MB-231, MDA-MB-361, MDCK II, MG63, MOR/0.2R, Mono-Mac-6, MRC-5, MTD-1A, MyEnd (Cellosaurus MyEnd CVCL_2131), NCI-H69, NCI-H69/CPR, NCI-H69/LX10, NCI-H69/LX20, NCI-H69/LX4, Neuro-2a, NIH-3T3, NALM-1, Neuro2a, NK-92, NTERA-2, NW-145, OKOPCN/OPCT cell lines, P3X63Ag8, PC12, Peer, PNT1A, PNT2, Pt K2, Raji, RBL-1, RenCa, RIN-5F, RMA-S, S2, Sf21, Sf9, SiHa, SK-BR-3, SK-OV-3, T2, T84, T98G, U373, U937, VCaP, Vero, VG-1, WM39, WT-49, YAC-1 and YAR cells.

Expression Vectors

In some embodiments, bacterial expression vectors, such as inducible T7 FLEXI vectors can be used designed for expression of Haloenzyme in bacterial cells. Bacterial expression vectors suitable for use with the present invention are commercially available and can include, for example, pF1A T7 Flexi, pF1K T7 Flexi, pFC20A HaloTag T7 SP6 Flexi, pFC20K HaloTag T7 SP6 Flexi, pFC27A HaloTag CMV-neo Flexi, pFC27K HaloTag CMV-neo Flexi, pFC30A His6HaloTag T7 Flexi, pFC30K His6HaloTag T7 Flexi, pFN18A HaloTag T7 Flexi, pFN18K HaloTag T7 Flexi, pFN19A HaloTag T7 SP6 Flexi, pFN19K HaloTag T7 SP6 Flexi, pFN21A HaloTag CMV Flexi, pFN21K HaloTag CMV Flexi, pFN22A HaloTag CMVd1 Flexi, pFN22K HaloTag CMVd1 Flexi, pFN23A HaloTag CMVd2 Flexi, pFN23K HaloTag CMVd2 Flexi, pFN24A HaloTag CMVd3 Flexi, pFN24K HaloTag CMVd3 Flexi, pFN28A HaloTag CMV-neo Flexi, pFN28K HaloTag CMV-neo Flexi, pH6HTC His6HaloTag T7, pH6HTN His6HaloTag T7, pHTC HaloTag CMV-neo, pHTN HaloTag CMV-neo. In some embodiments expression vectors can be used for the expression of Haloenzyme in yeast cells.

Haloenzyme (C-terminal) mammalian expression vectors are designed for expression of C-terminal-tagged Haloenzymes in mammalian cells. In some embodiments the expression vector can be a C-terminal-tagged mammalian expression vectors suitable for use with the present invention are commercially available and can include, for example, pFC14A HaloTag CMV, pFC14K HaloTag CMV, pFC15A HaloTag CMVd1, pFC15K HaloTag CMVd1, pFC16A HaloTag CMVd2, pFC16K HaloTag CMVd2, pFC17A HaloTag CMVd3, pFC17K HaloTag CMVd3, pFC27A HaloTag CMV-neo, pFC27K HaloTag CMV-neo, and pHTC HaloTag CMV-neo Vector.

Haloenzyme Fusion (N-terminal) mammalian expression vectors are designed for expression of N-terminal-tagged Haloenzymesin mammalian cells. In some embodiments the expression vector can be a N-terminal-tagged HaloTag fusion mammalian expression vectors suitable for use with the present invention are commercially available and can include, for example, pHTN HaloTag CMV-neo Vector, pFN28A HaloTag CMV-neo, pFN28K HaloTag CMV-neo, pFN21A HaloTag CMV, pFN21K HaloTag CMV, pFN22A HaloTag CMVd1, pFN22K HaloTag CMVd1, pFN23A HaloTag CMVd2, pFN23K HaloTag CMVd2, pFN24A HaloTag CMVd3, and pFN24K HaloTag CMVd3.

Haloenzymes expression vectors can be used in *E. coli* and cell-free systems using the T7 RNA polymerase promoter. In some embodiments the expression vector can be an *E. coli* and cell-free system compatible expression vector can include, for example, pH6HTC His6HaloTag T7, pH6HTN His6HaloTag T7, pFN29A His6HaloTag T7, pFN29K His6HaloTag T7, pFC30A His6HaloTag T7, pFC30K His6HaloTag T7, pF1A T7, pF1K T7, pFN18A HaloTag T7, pFN18K HaloTag T7, pFN19A HaloTag T7 SP6, pFN19K HaloTag T7 SP6, pFC20A HaloTag T7 SP6 and pFC20K HaloTag T7 SP6.

In some embodiments, the expression vector can be pERB217 and Halo-GFP-mitochondrial fission factor (Mff) vectors, as described herein.

In some embodiments, the expression vector can direct the localization of the Haloenzyme to any cellular compartment by fusion to a compartment-specific protein or tag sequence, thereby enabling specific relative quantitation of access of an agent to any compartment or organelle. Examples of membrane-bound cellular compartments or cellular organelles can include the cytoplasm, endosome, endoplasmic reticulum, golgi apparatus, lysosomes, microtubules, mitochondria (e.g, mitochondrial matrix), mitochondrial intermembrane space, nucleus, peroxisomes, perinuclear recycling compartment, ribosomes or any other compartment or localized area with a cell.

Haloligand Functional Groups

In some embodiments the Haloligand functional groups can include fluorescent functional groups. Cell permeant fluorescent functional groups suitable for use with the present invention are commercially available and include, for example, HaloTag TMR (tetramethyl rhodamine); HaloTag TAMRA (tetrazine-tetramethylrhodamine), HaloTag Oregon Green, HaloTag diAcFAM, and HaloTag Coumarin. The permeant ligands cross the cell membrane and, therefore, can be used to label intracellular proteins. Cell impermeant functional groups are commercially available and include, for example, HaloTag Alexa Fluor 488 and HaloTag Alexa Fluor 660. The impermeable fluorescent functional groups can be used to label cell surface proteins. Additional Haloligands that can be used in for detection, HaloTag TMRDirect, HaloTag R110Direct, HaloTag Biotin and HaloTag PEG-Biotin.

In some embodiments the Haloligand functional group can include functional groups containing a metal atom. In some embodiments, the metal atom of the Haloligand functional group is magnetic. Magnetic Haloligands can include, for example, Magne HaloTag beads. In some embodiments the metal atom Haloligand can include, for example, an atom, ion, or isotope with a specific mass spectrometric signature for detection by atomic absorption, mass spectrometry, or nuclear magnetic resonance (NMR).

Chloroalkane Penetration Assay (CAPA)

In an embodiment, molecules are localized and quantified using the Chloroalkane Penetration Assay (CAPA) method. In some embodiments, the CAPA method uses a cell line that stably expresses a cytosolically-oriented fusion protein configured with green fluorescent protein (GFP) and HaloEnzyme. In some embodiments, the CAPA method uses a cell line that stably expresses a cytosolically-oriented fusion protein configured HaloEnzyme. The GFP can be used to verify the stable expression, relative amount, and subcellular localization of the fusion protein. The HaloEnzyme expressed within the cell is a modified bacterial chloroalkane dehalogenase that covalently labels itself with the small, otherwise inert Haloligand (Lang et al., Los et al., Friedman, et al.). Therefore, if an exogenously added molecule conjugated to a Haloligand (e.g., bearing a chloroalkane group) penetrates the cellular plasma membrane and reaches the cytosol, it reacts exclusively with the HaloEnzyme and blocks its active site. Following this incubation period, the amount of unreacted HaloEnzyme was measured by chasing with a Haloligand conjugated with a fluorescent functional group (e.g., HTag-TAMRA). The relative amount of cellular fluorescence after the chase procedure can then quantified by flow cytometry. The fluorescent signal reports directly on the amount of free HaloEnzyme, which is inversely proportional to the degree to which the added molecule accessed the cytoplasm during the incubation period. A schematic of the CAPA method is illustrated in FIG. 1A, wherein the molecule of interest is a peptide.

The CAPA method confers many advantages over existing quantification methods. The CAPA method can be directly applied to any chemically tractable molecule, for example, small molecules, peptides, proteins, nucleic acids, antibodies, viral particles, and nanoparticles. Since the CAPA method introduces the HaloEnzyme genetically, it can be directed to any cellular compartment, enabling specific relative quantitation of access to any compartment or organelle. Many other cell penetration methods cannot reliably distinguish between molecules trapped in endosomes or other vesicles, and thus cannot selectively measure penetration to the cytoplasm. The reliability of genetically dictating the location of the Haloenzyme fusion within the cell makes the signal from CAPA an exclusive reporter of localization to the desired compartment (i.e., the cytoplasm) without interference from material trapped in other compartments (i.e., endosomes or other vesicles). The CAPA method does not require labeling with large perturbing tags (e.g., high molecular weight aromatic and fluorescent dyes), but only a smaller, less-perturbing tag containing the chloroalkane group.

In some embodiments, CAPA can be applied to cell lysates of cells contacted with an agent or molecule of interest, as described above, in place of flow cytometry. The cell lysate can be fractionated or whole cell lysate. The cell lysate can be used to measure levels of agent or molecule of interest by the described herein, for example, atomic absorption, mass spectrometry, fluorescence, nuclear magnetic resonance (NMR), or any standard method.

The practice of the present invention employs, unless otherwise indicated, conventional techniques of molecular biology (including recombinant techniques), microbiology, cell biology, biochemistry and immunology, which are well within the purview one of ordinary skill in the art. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Chloroalkane Penetration Assay (CAPA): A New Assay for Measuring Relative Cytosolic Access A novel cell penetration assay was developed to quantify the cytosolic delivery of a stapled peptide DD5-o, which induces autophagy. It was important to verify that DD5-o reaches the cytosol and to quantify the relative extent of cytosolic delivery without interference from endosomally trapped peptide. Due to the small size and relative hydrophobicity of the peptide, and due to the sensitivity of the structure activity relationships, it was desirable to avoid using large perturbing tags such as fluorescent dyes. For these reasons a novel cell penetration assay was developed to quantify the cytosolic delivery of DD5-o. The assay, called Chloroalkane Penetration Assay (CAPA), is inexpensive, quantitative, high-throughput, does not require labelling with large aromatic dyes, and can be adapted for measuring access to any cellular compartment (FIG. 1A).

The CAPA method uses a cell line that stably expresses a cytosolically-oriented protein as a fusion with GFP and Haloenzyme. Haloenzyme is a modified bacterial chloroalkane dehalogenase that covalently labels itself with the small, otherwise inert Haloligand functional group. If an exogenously added molecule bearing the Haloligand (a small chloroalkane) reaches the cytosol, it reacts exclusively with the Haloenzyme and blocks its active site. Following this incubation period, the amount of unreacted Haloenzyme was measured by chasing with a Haloligand-bearing dye (here, Htag-TAMRA). The relative amount of red cellular fluorescence after this chase was then quantified by flow cytometry. The red signal reported directly on the amount of free Haloenzyme, which is inversely proportional to the degree to which the added molecule accessed the cytoplasm during the incubation period.

Figure 1B:
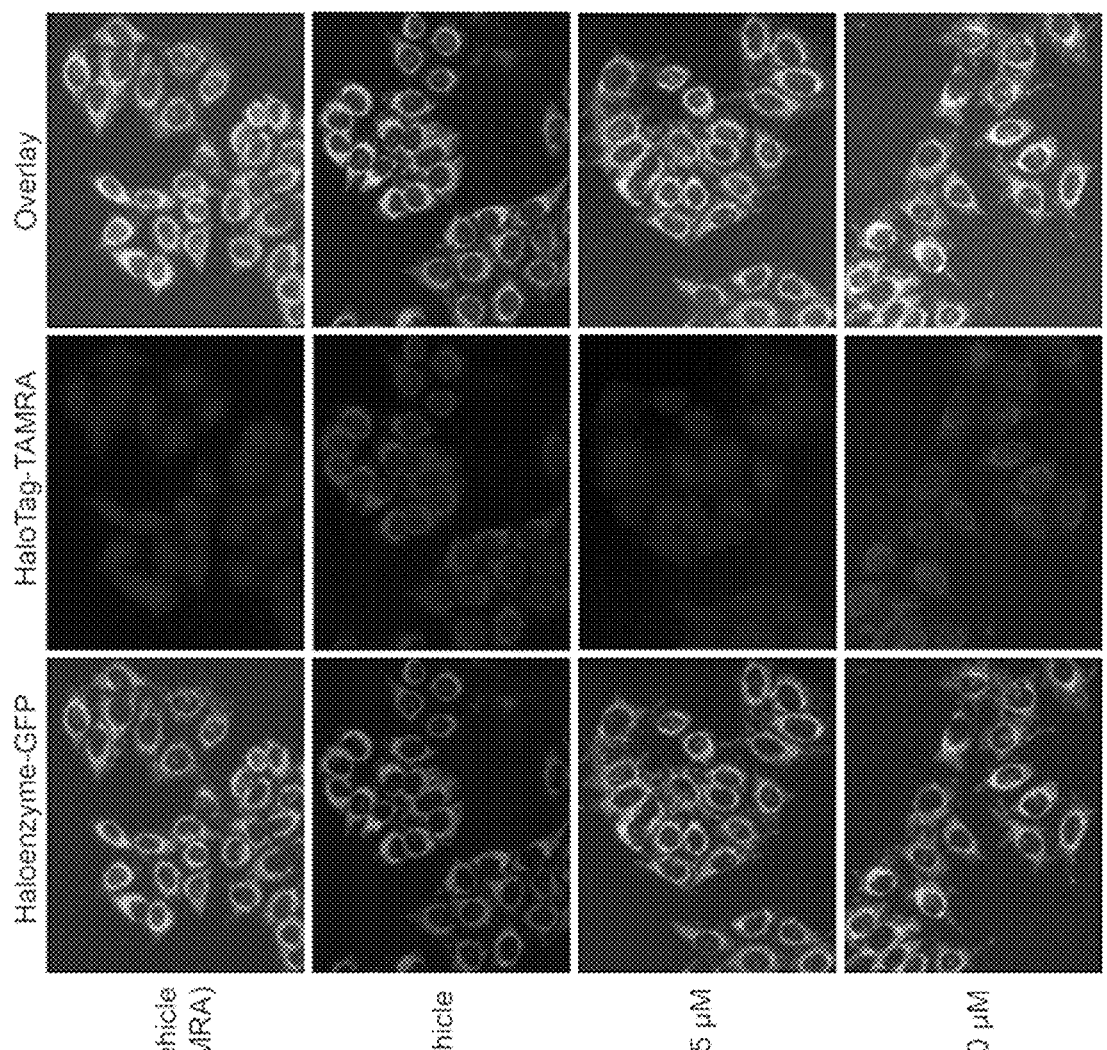
Figure 1C:
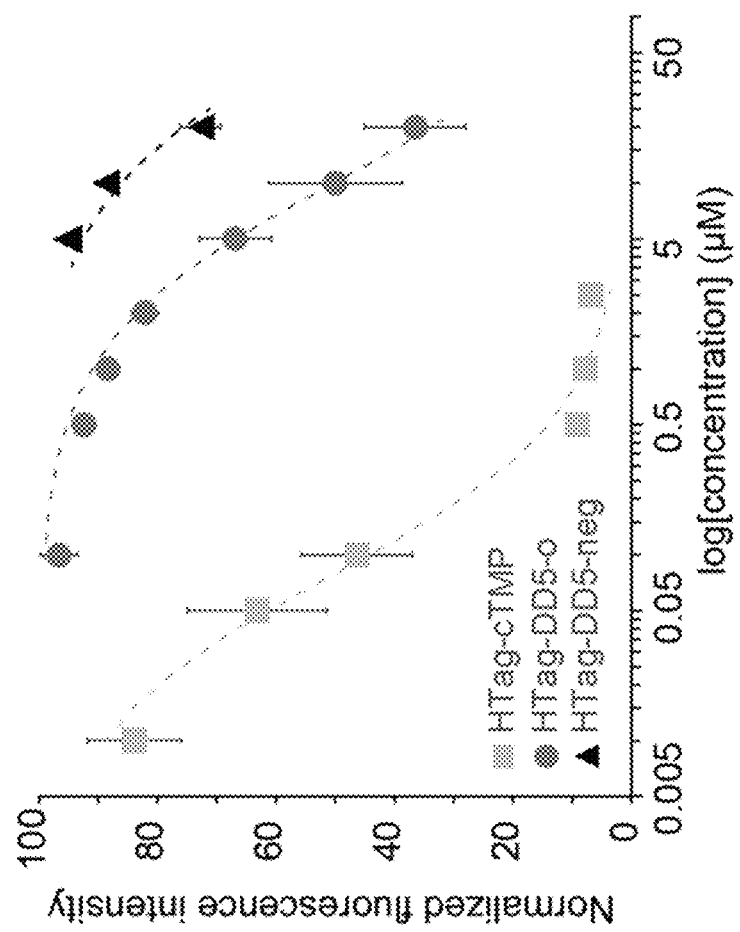
Figure 1D:
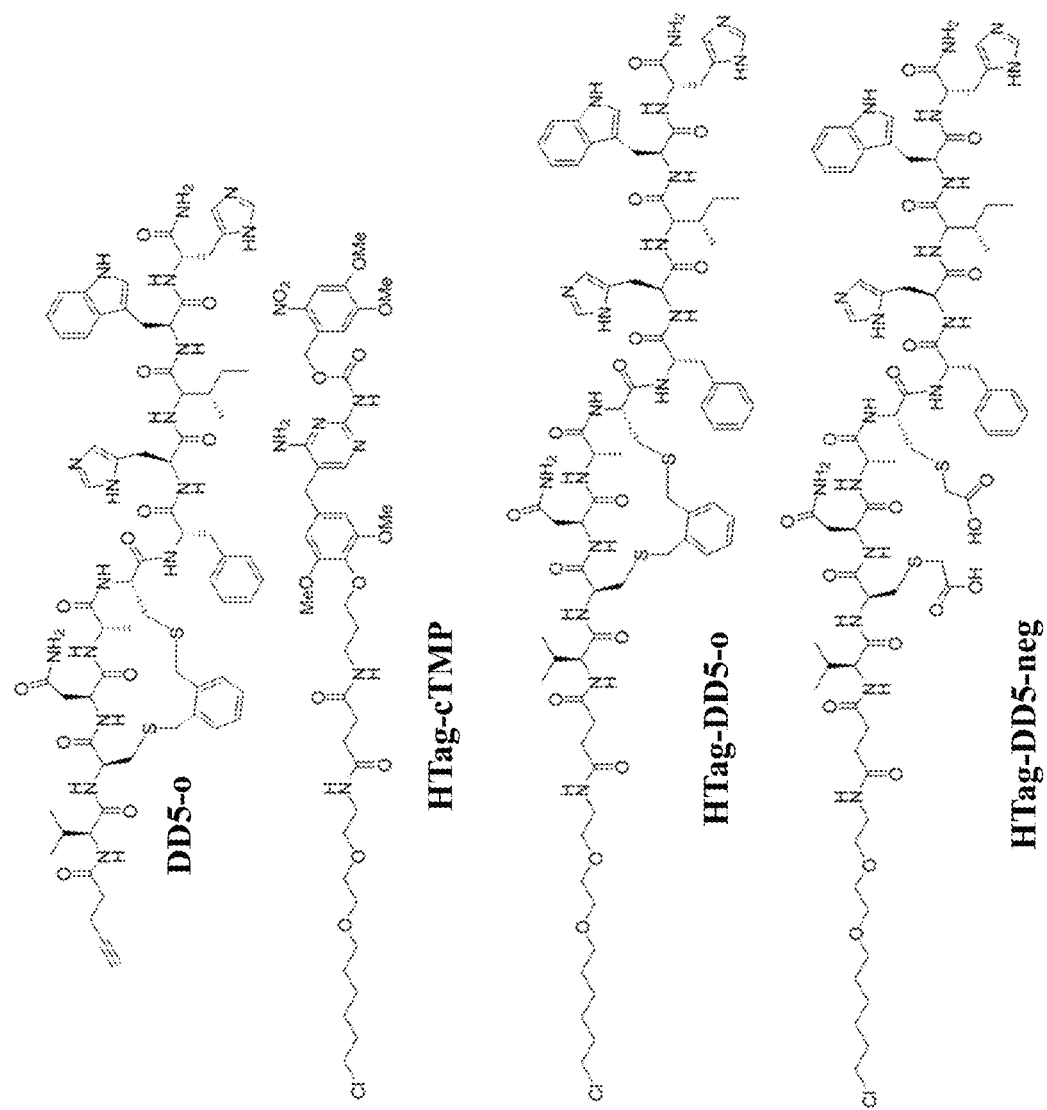
Figure 2A:
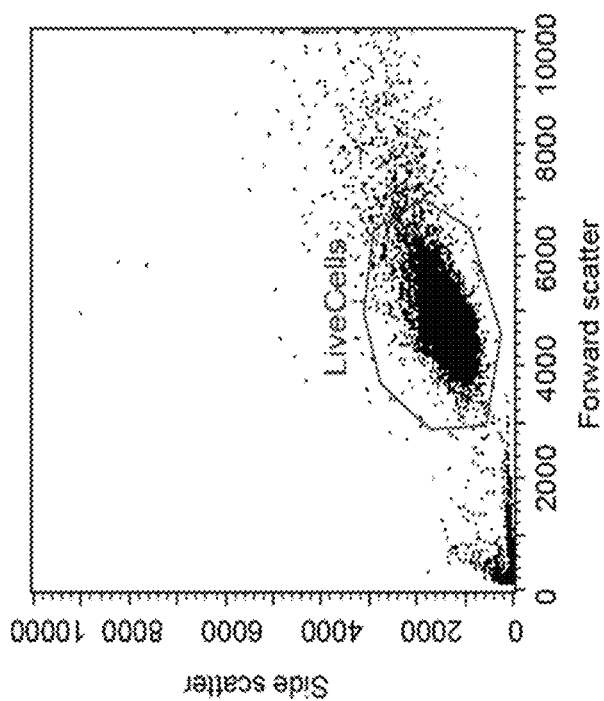
FIGS. 2A-2D provides a series of graphs showing flow cytometry data from CAPA. These plots show a representative replicate of raw data obtained from CAPA.
Figure 2B:
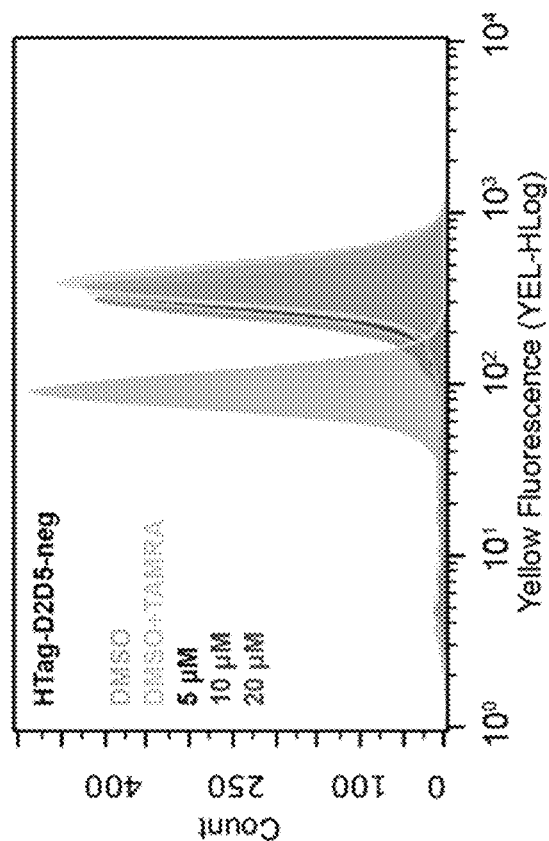
Figures 2C, 2D:
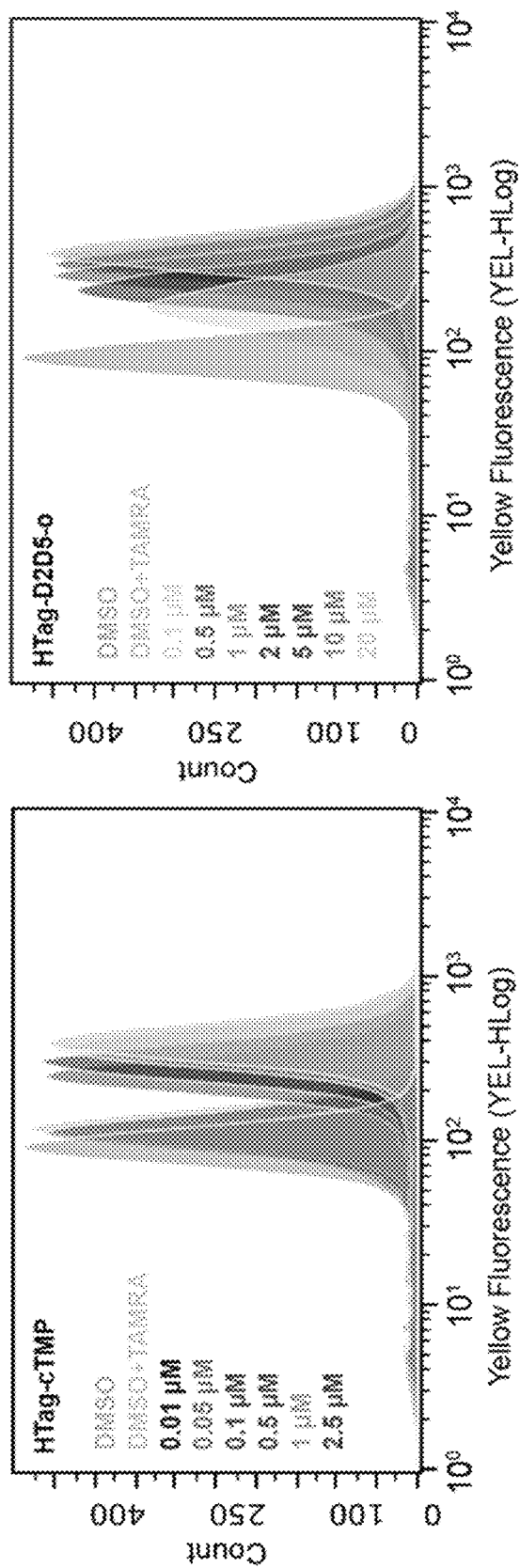

CAPA was evaluated with HTag-cTMP, a small molecule previously used as a tool for cytosolic protein localization. As quantified by flow cytometry, inhibition of the fluorescent HTag-TAMRA (e.g., Haloligand conjugated tetrazine-tetramethylrhodamine) signal was observed when cells were pre-incubated with HTag-cTMP, and this inhibition was dose-dependent with respect to amount of the HTag-cTMP used in the pre-incubation step. Fluorescence microscopy confirmed that the HTag-TAMRA colocalized with the cytosolically oriented GFP-HaloEnzyme, and that pre-incubation with HTag-cTMP suppressed up to 90% of the HTag-TAMRA signal (FIG. 1B). HTag-DD5-o, in which the DD5-o sequence is capped with the Haloligand, was synthesized, and LC3 and p62 immunoblot assays verified that it increased autophagy similarly to the original DD5-o polypeptide. In CAPA, HTag-DD5-o produced dose-dependent suppression of the HTag-TAMRA signal (FIG. 1B and FIG. 1C). Its dose-dependence curve was similar in shape to HTag-cTMP, but was shifted 100-fold higher in concentration, as expected for a peptide relative to a small molecule (FIG. 1C). A negatively charged, linear variant was also tested, which exhibited cytosolic entry only at very high concentrations and at the limit of solubility (FIG. 1C). Thus, the rapid, inexpensive CAPA method confirmed the cytosolic localization of HTag-DD5-o at micromolar concentrations, which correlates with the concentrations at which it activates autophagy.

CAPA does not require large, hydrophobic dyes, just a small chloroalkane tag. Because the HeLa cells stably express Haloenzyme fused to a cytosolically-oriented protein domain, any signal dependent on the Haloenzyme reports exclusively on cytoplasmic access of the Haloligand-bearing molecule. When the Haloligand-bearing molecule of interest enters the cell, it covalently reacts with cytoplasmic Haloenzyme and blocks subsequent reaction with the Haloligand-bearing dye in the next step. Control experiments revealed that up to 90% of the overall signal could be suppressed by pre-incubation with a cell-penetrant, Haloligand-conjugated small molecule. The remaining 10% is likely due to Haloenzyme expressed during the subsequent dye incubation and wash steps. The signal was measured using a benchtop flow cytometer. Other readouts are feasible, but flow cytometry provided high-quality, quantitative data in an inexpensive and high-throughput format.

CAPA allowed direct assessment of the dose-dependence of cell penetration for DD5-o. Importantly, this dose dependence closely matches the dose-dependence of autophagy induction. These data imply that potency is currently limited by cell penetration, and that improving cell penetration will improve overall activity. The ability to quantitate cell penetration in a high-throughput manner will greatly accelerate development of these and other potential peptide therapeutics. In fact, the CAPA method can be directly applied to any chemically tractable molecule, including small molecules, peptides, proteins, nucleic acids, antibodies, viral particles, and nanoparticles. Because the Haloenzyme is genetically introduced, it can be directed to any cellular compartment, enabling specific relative quantitation of access to any compartment or organelle.

Example 2—Protocol for Labeling a Molecule with Chloroalkane Ligand

Figure 4:
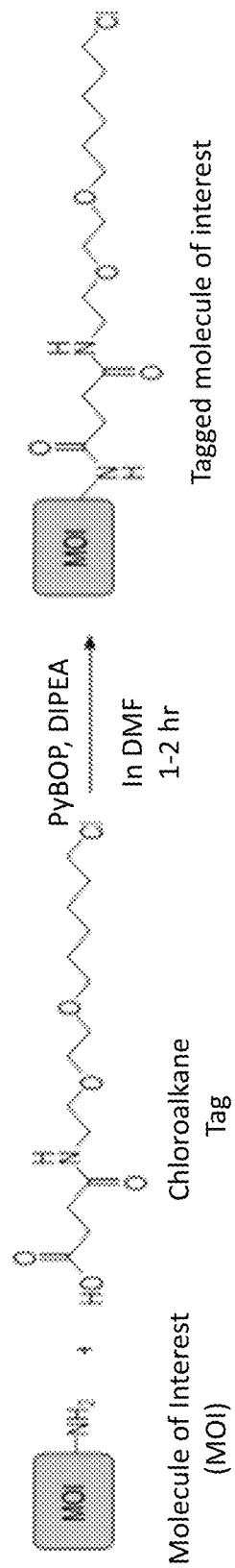
FIG. 4 provides a schematic for the protocol for labeling an agent or molecule of interest with a Haloligand (e.g., chloroalkane tag).

The following protocol was utilized to label molecules with a chloroalkane ligand. First three equivalents of the chloroalkane ligand was dissolved in dry dimethylformamide (DMF), followed by the addition of three equivalents of the coupling reagent benzotriazol-1-yl-oxytripyrrolidino-phosphonium hexafluorophosphate (PyBOP). The solution was then mix until all components were dissolved. The molecule of interest (MOI) containing a free amine was then added to the mixture. Next, six equivalents of N, N-Diisopropylethylamine (DIPEA) was added and stirred at room temperature for 1-2 hours. The molecule of interest was then purified with an appropriate method, for example, Reversed Phase-High Performance Liquid Chromatography (RP-HPLC) to separate out unreacted ligand and coupling reagent. FIG. 4 provides a simplified schematic of the chemical reaction for labeling a molecule of interest with chloroalkane ligand.

Example 3—Application of the CAPA for Cell Penetration Profiling

In the experiments described in this example, CAPA was used to provide a cell penetration profile for several classes of cell-penetrating biomolecules. The cell penetration profile included a direct measurement of many aspects of cell penetration, including the extent of penetration, time course, dose dependence, penetration to different subcellular compartments, and mechanisms of endocytic uptake, endosomal escape, and nuclear import.

Cell Penetration Profiling of a Variety of Biomolecules

Figure 5A:
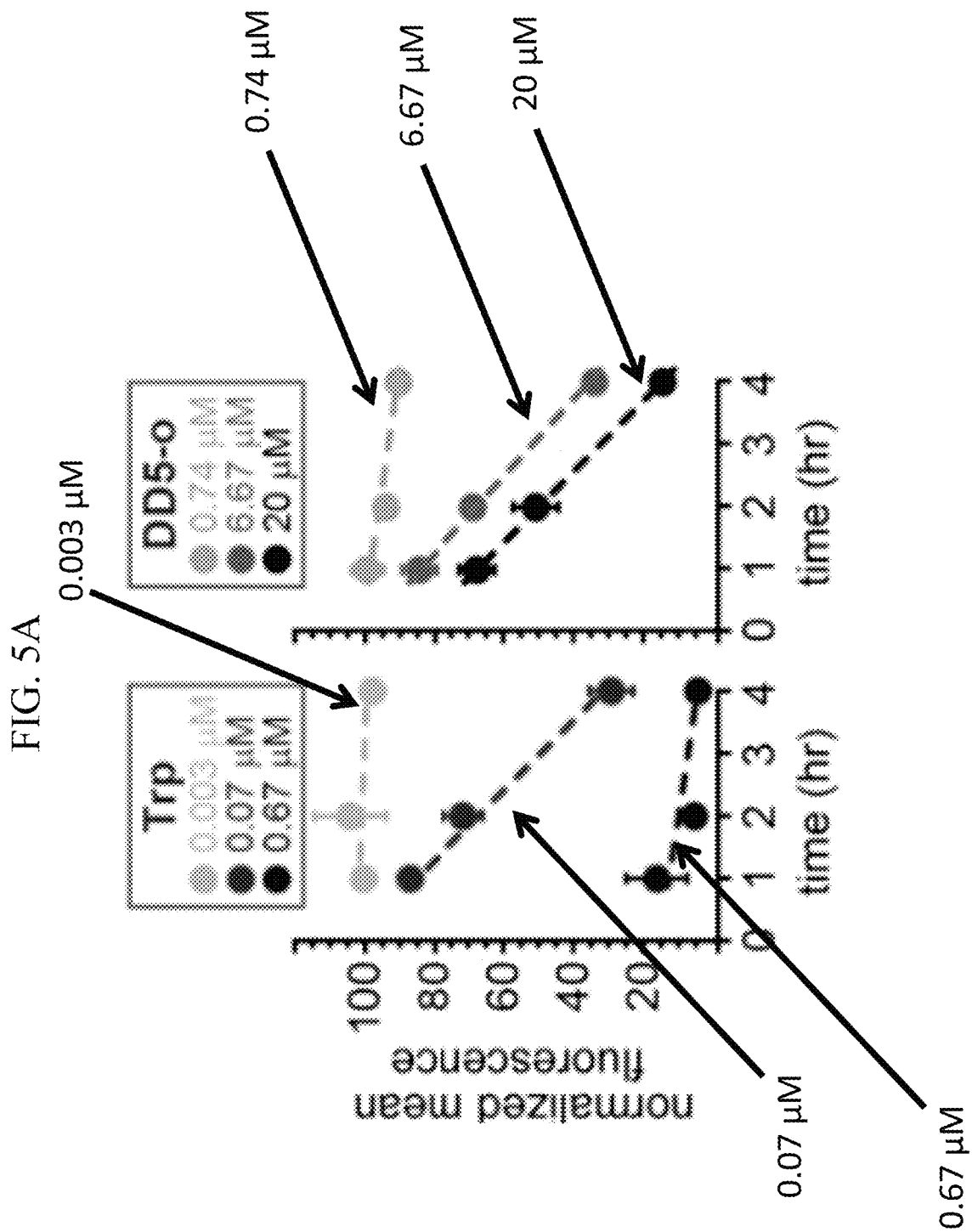
FIG. 5A, FIG. 5B, FIG. 5C, and FIG. 5D show graphs of cell penetration profiling.
Figure 5B:
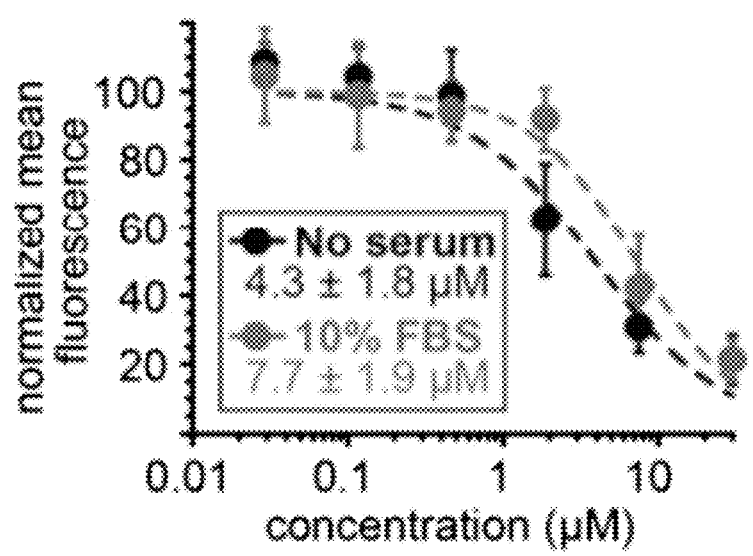
Figure 5C:
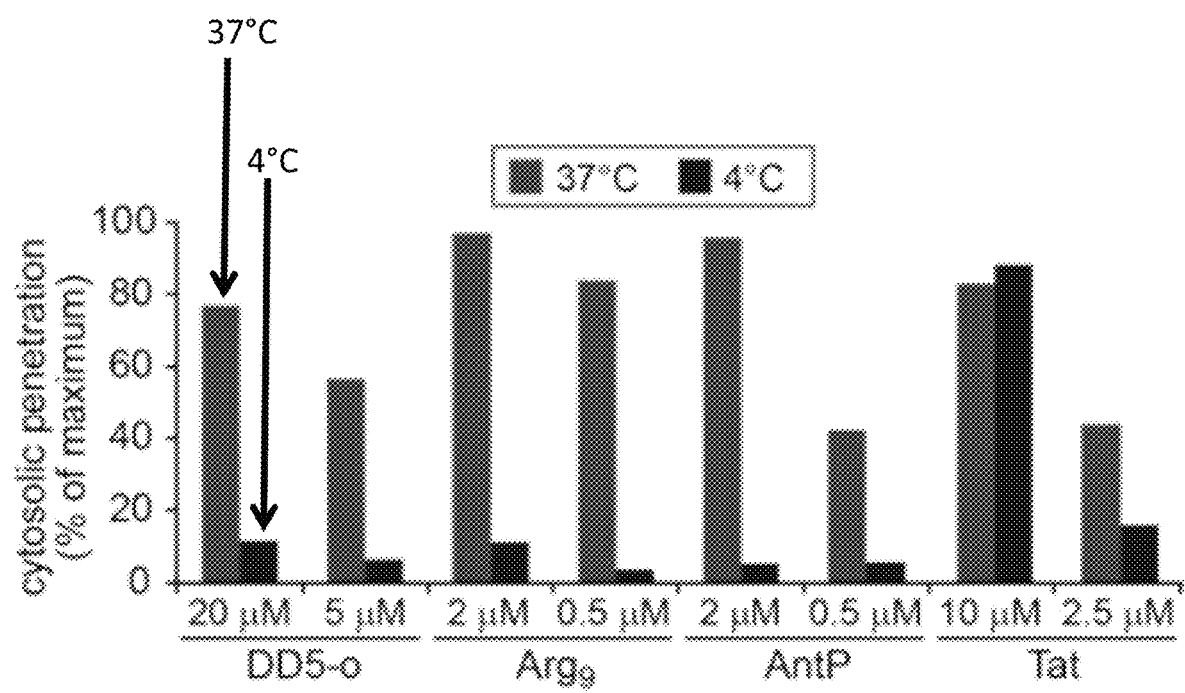
Figure 5D:
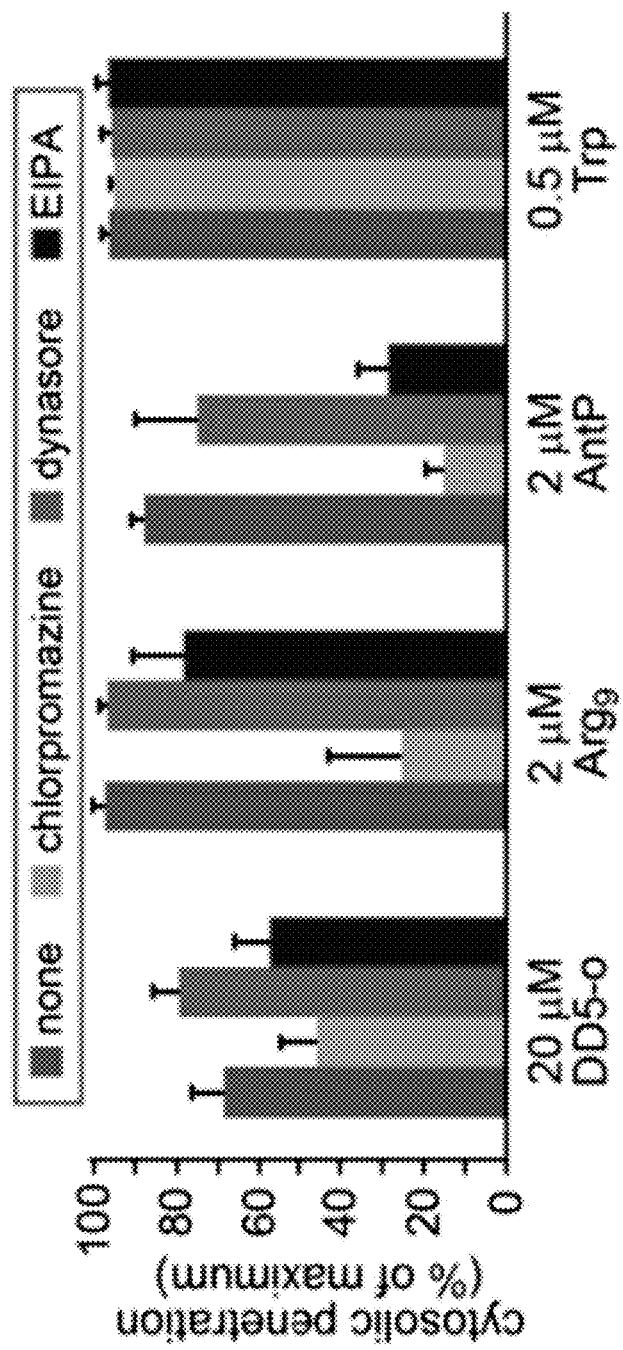

CAPA was used to analyze the cell penetration profile of several biomolecules, including a stapled peptide (DD5-o), a small molecule (Trp), and several polycationic peptides ($Arg_9$ (SEQ ID NO: 5)), AntP, and Tat) (FIG. 5A, FIG. 5B, FIG. 5C). The time course of cytosolic penetration for DD5-o and Trp is shown in FIG. 5A. These results indicate time-dependent cytosolic penetration for both these molecules, with a greater extent of penetration for the small molecule compared to the peptide, as expected. FIG. 5B shows the effect of serum on cytosolic penetration for DD5-o. Demonstrating the effect of serum on overall cell penetration has been difficult in the past, but CAPA reveals a slight decrease in cell penetration in the presence of serum, as expected, and with excellent resolution and reproducibility. The effect of cytosolic penetration at two different temperatures (4° C. and 37° C.) for DD5-o, $Arg_9$ (SEQ ID NO: 5), AntP, and Tat was compared in FIG. 5C. For each biomolecule in FIG. 5C, at nearly every concentration the cytosolic penetration was significantly greater at 37° C. compared to 4° C. Such data is commonly interpreted as implying that cell penetration is an energy-dependent process, which is expected for the peptides and less so for the small molecule. In FIG. 5D, the effect of several endocytosis inhibitors on cytosolic penetration was tested. The endocytosis inhibitors included chlorpromazine, dynasore, and EIPA. Chlorpromazine significantly reduced cytosolic penetration in each tested biomolecule except Trp, where it had no effect. This is consistent with an energy-dependent endocytosis mechanism of uptake for the peptides, and an energy-independent, passive mechanism of uptake for the small molecule. The dynasore inhibitor did not significantly affect cytosolic penetration compared to the 'no inhibitor' control. In addition, the EIPA inhibitor significantly reduced cytosolic penetration for AntP, but no significant reduction in cytosolic penetration was observed for DD5-o, $Arg_9$ (SEQ ID NO: 5), or Trp. These results provide insight into the types of endocytosis involved for penetration of each of these peptides, since dynasore inhibits dynamin, a protein critical for clathrin-mediated endocytosis; chlorpromazine also inhibits clathrin-mediated endocytosis, but using a different mechanism than dynasore; EIPA inhibits a different endocytosis pathway called macropinocytosis. This data demonstrates the use of CAPA to investigate the cellular mechanisms that a variety of different biomolecules use to penetrate the cell.

Based on the results described above for the DD5-o, Trp, $Arg_9$ (SEQ ID NO: 5), AntP, and Tat biomolecules, CAPA and the above described methods are suitable to analyze the cell penetration profile of additional biomolecules, such as those listed in Table 1 below.

TABLE 1

Molecules for benchmarking CAPA.

| Name | Type of molecule | Refs |
|---|---|---|
| Tat | Polycationic peptide | 1, 2, 3 |
| $Arg_9$ (SEQ ID NO: 5) | Polycationic peptide | 1, 2, 3 |
| AntP | Polycationic peptide | 4, 5 |
| ZF5.3 | Polycationic structured peptide | 6, 7 |
| CLIP6 | Polycationic unstructured peptide | 8 |
| $cF\Phi R_4$ | Polycationic bicyclic peptide | 7, 9 |
| CPP12 | Polycationic bicyclic peptide | 7 |
| BIM-SAHB$_{A1}$ | Hydrocarbon-stapled peptide | 10, 11, 12 |
| ATSP-7041 | Hydrocarbon-stapled peptide | 13 |
| DD5-o | Thioether-stapled peptide | 14 |
| Lin8 | Thioether-stapled peptide | 15 |
| Trp | Small molecule (amino acid) | |
| SAHA | Small molecule | 16, 17 |
| Dasatinib | Small molecule | 16, 18 |
| cTMP | Small molecule | 14, 19 |

The molecules listed in Table 1 include small molecules, four classes of polycationic peptides, and two classes of stapled peptides. CAPA provides results related to each biomolecule's cell penetration properties by (1) time course experiments, such as comparing each of the following time points: 5, 30, 60, 120, and 240 min at 0.01, 0.033, 0.1, 0.33, 1.0, 3.3 and 10 μM concentrations; (2) the effects of serum versus serum-free medium; (3) the effects of 4° C. and 37° C. incubations; (4) the effects of endocytosis inhibitors including beta-cyclodextran, nystatin, EIPA, chlorpromazine, and dynasore; (5) and the effects of endocytosis enhancers, such as high salt and propane betaine. Comparing effects of time, temperature, and specific endocytosis inhibitors will provide data on a biomolecule's mechanism of cytosolic penetration, and its dependence on cellular energy, specific endocytosis pathways, and specific modes of endosomal leakage.

Profiling Penetration to Cellular Compartments

Figure 6A:
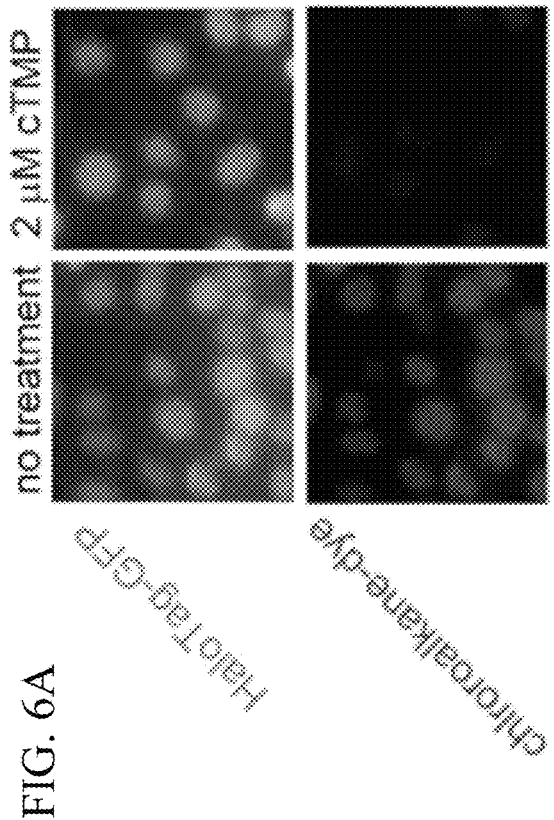
FIG. 6A, FIG. 6B and FIG. 6C shows graphs and images of penetration profiling to cellular compartments using HaloTag fusion proteins.
Figure 6B:
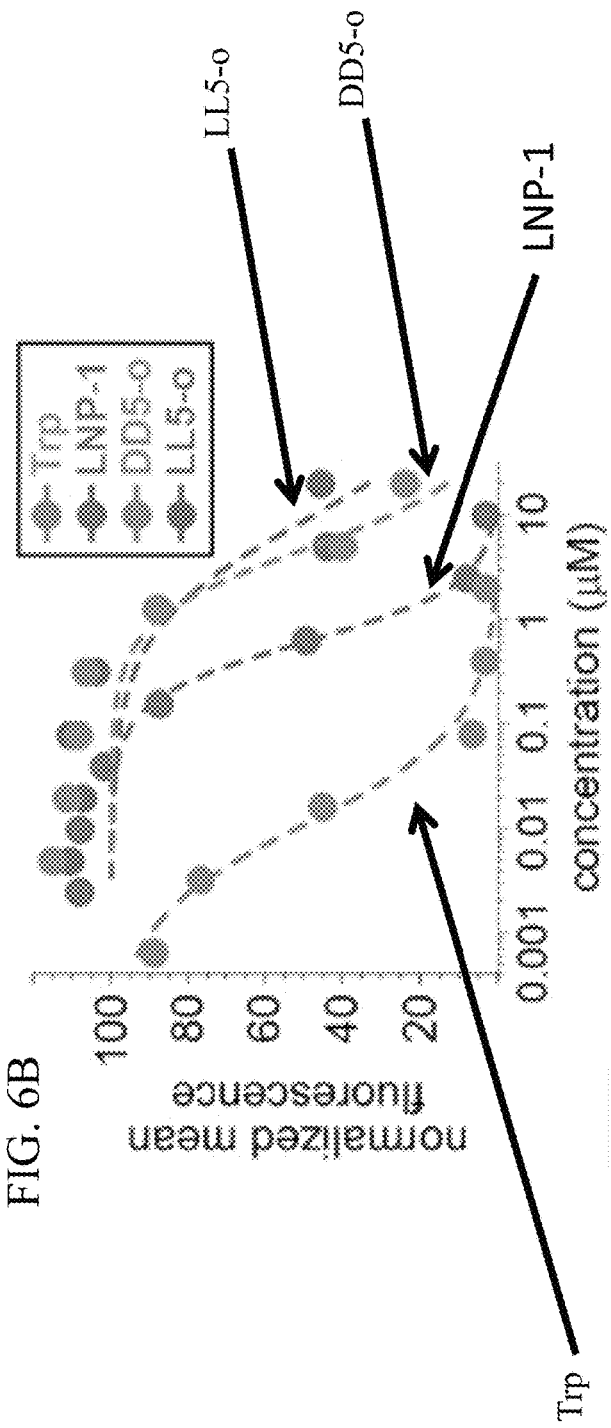

CAPA can be used to assess the penetration of a variety of different biomolecules into specific organelles and cellular compartments (e.g., the cytosol, nucleus, ER, Golgi, mitochondrial matrix, lysosome, or endosome). In one experiment, the cellular penetration of cTMP, TRP-1, DD5-o, and LL5-o biomolecules into the nucleus was examined (FIG. 6A, FIG. 6B). Initially, a HeLa cell line was generated using the HaloTag system that stably expressed a nuclear-oriented protein as a fusion with GFP and a modified bacterial chloroalkane dehalogenase ("HaloTag-GFP"). To localize the HaloTag-GFP to the nucleus in HeLa cells, the HaloTag-GFP molecule was fused to Histone H2B, which localizes to the nucleus (top left image of FIG. 6A).[22] Cells were then treated exogenously with 2 μM of the Haloligand-containing small molecule cTMP, which reacted exclusively with the HaloTag-GFP localized in the nucleus. To demonstrate nuclear penetration, cells were treated with 2 μM of the Haloligand-containing small molecule cTMP, which blocked over 90% of the signal of a chloroalkane dye (compare bottom left and bottom right images). This experiment demonstrated that the Haloligand-containing small molecule cTMP was able to penetrate the nucleus of the HeLa cell line.

Figure 6C:
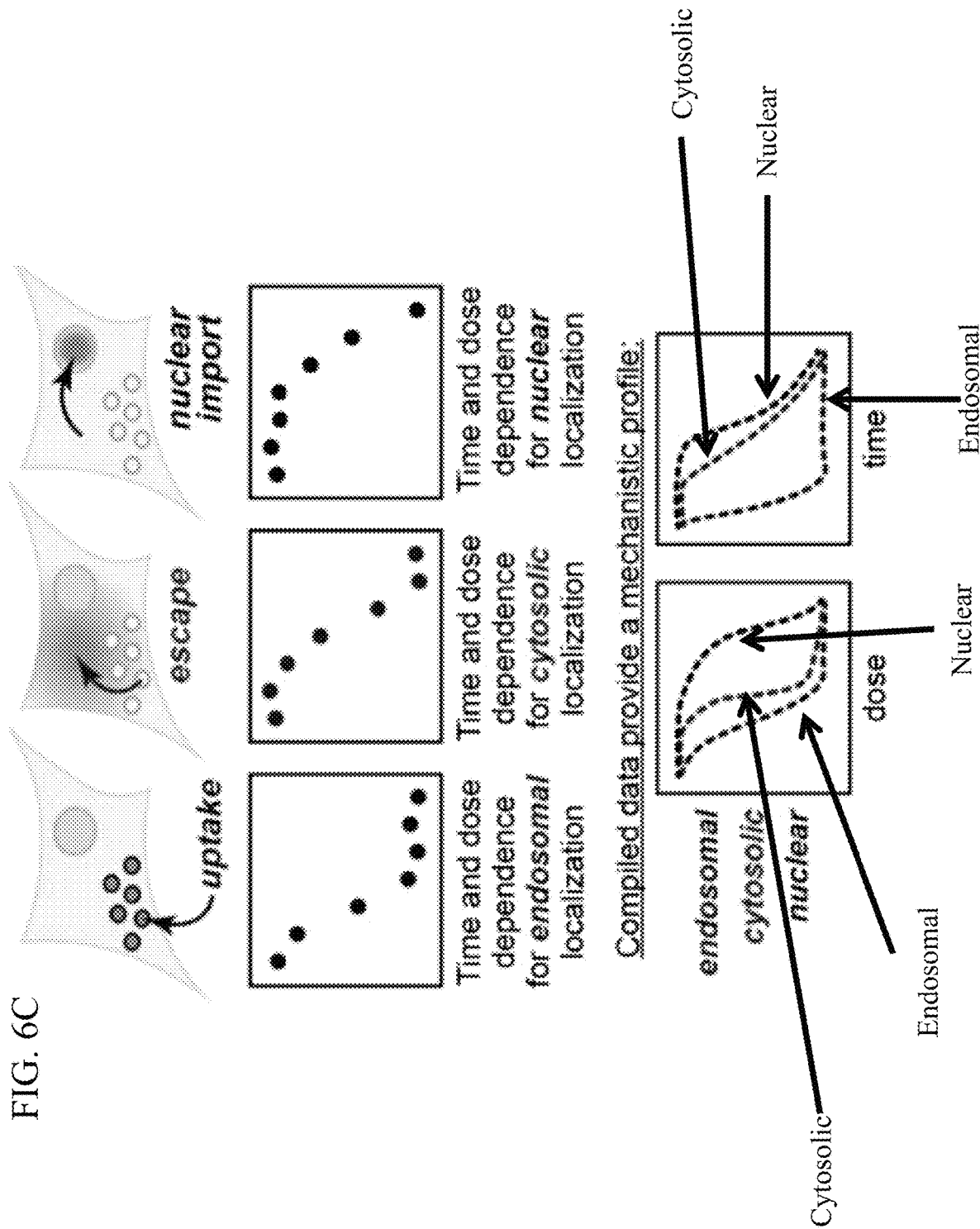

The HeLa cells that stably expressed HaloTag-GFP in the nucleus were also used to profile dose dependencies of nuclear penetration for other biomolecules (FIG. 6B). The biomolecules in FIG. 6B include the small molecule Trp, the lipid nanoparticle LNP-1, as well as the peptides DD5-o, and LL5-o. These data show the dose dependencies of penetration of these molecules specifically to the nucleus (FIG. 6B). FIG. 6C provides an illustration of profiling molecules with different penetration mechanisms based on time and dose dependency for endosomal, cytosolic, and nuclear localization. Biomolecules with different entry mechanisms into specific organelles and cellular compartments are expected to have different profiles, as depicted in FIG. 6C and demonstrated in the experiments described herein.

Cell Penetration Profiling for Nucleic Acid Therapeutics and Nanoparticle Delivery Currently, a significant barrier for nucleic acid therapeutics is intracellular delivery of molecules and trafficking to organelles and cellular compartments.[3] Antisense oligonucleotides (ASOs) represent an emerging class of nucleic acid therapeutics. ASOs are typically 18-30 base pairs long, with phosphorothioates substituted for phosphates to reduce nuclease susceptibility and to increase protein binding, which prolongs ASO half-life in vivo. ASOs are also typically 2'-modified with fluoro, methoxy, or O-methoxyethyl groups, or they can be cyclized between the 2' and 4' positions ("locked nucleic acids").[22] Several ASOs have been tested in animal models and clinical trials, and some are FDA-approved drugs. However, many challenges remain for their preclinical and clinical development that makes the design of cell penetrating ASO-based delivery systems difficult. For example, such challenges include an inability to quantitate cytosolic penetration, to quantitate endosomal trafficking and escape, and the poor resolution of current microscopy-based methods for monitoring ASO trafficking. Also, the details regarding "productive" and "non-productive" pathways of internalization of ASOs are unclear.[8,9] Advantageously, CAPA is useful for evaluating the cell penetration of ASOs, such as those listed in Table 2 below.

TABLE 2

ASOs for evaluation using cell penetration profiling.

| Name | Length, modification | Target | Refs |
|---|---|---|---|
| ISIS-APO(a)$_{Rx}$ | 20-mer, 10 2'-O-methoxyethyl | Lp(a) | 17, 18 |
| ISIS 304801 | 20-mer, 10 2'-O-methoxyethyl | ApoC-III | 16, 17, 18 |
| ASO A | 20-mer, 10 2'-O-methoxyethyl | Ube3a-AT | 17, 18 |
| nusinersen | 18-mer, all 2'-O-methoxyethyl | SMN1 | 4, 19 |
| mongersen | 21-mer, 2 5-methylcytosines | SMAD7 | 4, 19-20 |

Each ASO listed in Table 2 has a complete replacement of phosphates with phosphorothioates (a mixture of stereoisomers), and each can be 5'-amine-modified to allow for conjugation of the chloroalkane group, similar to common strategies for dye attachment. Thus, the penetration of the ASOs in Table 2 (or any other ASOs or nucleic acid therapeutics) into specific organelles and cellular compartments can be evaluated using CAPA.

Figure 7A:
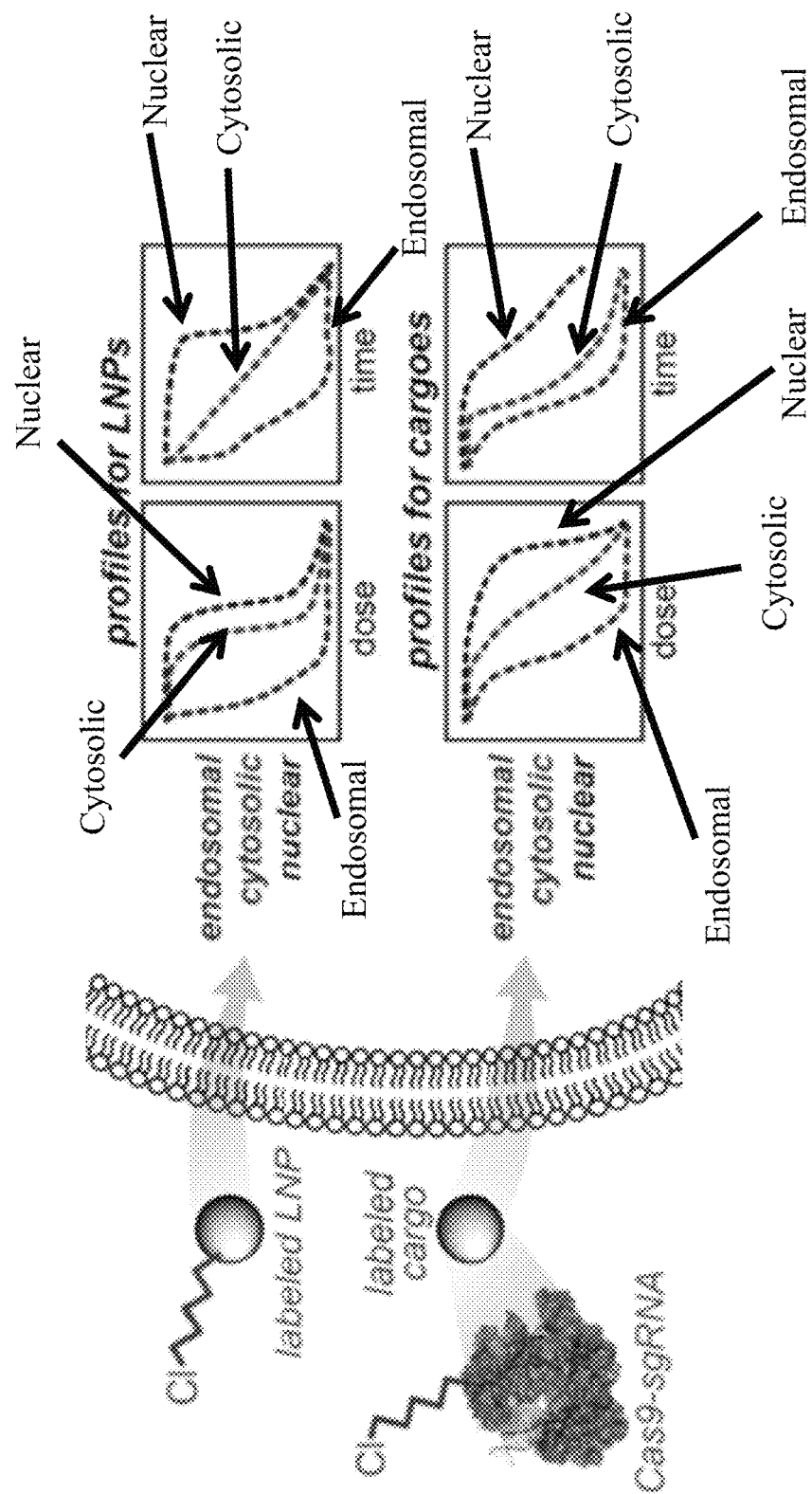
FIG. 7A and FIG. 7B are graphs and images showing cell penetration profiling for lipid nanoparticle (LNP) drug delivery.
Figure 7B:
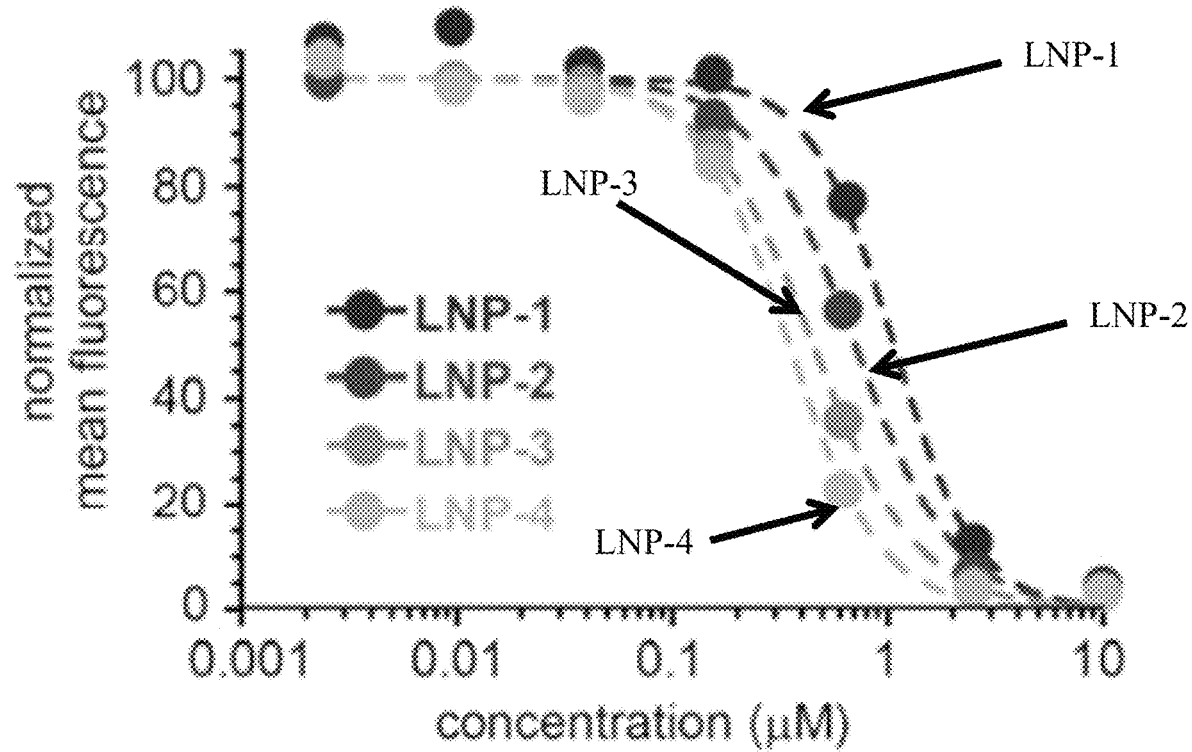

CAPA was also used to measure cell penetration of chloroalkane-functionalized lipid nanoparticles (LNPs) (FIG. 7A, FIG. 7B). LNPs are particularly suitable for delivering cargo (e.g., drugs, antibodies or other proteins) to cells or tissues. Prior to the present invention, nanoparticle-mediated drug delivery typically relied almost exclusively on fluorescence microscopy and phenotype to determine cell penetration. However, given the complex interplay among nanoparticles, their cargo, and the cell, CAPA provides a foundational advance to profile cell penetration. LNPs are cell-penetrant via endocytic uptake, but their endosomal escape pathways are poorly understood.[1] CAPA can elucidate dose dependence, time dependence, and mechanisms of uptake and endosomal escape for LNPs. As described herein, CAPA is used to measure cell penetration profiling of chloroalkane-functionalized lipid nanoparticles (LNPs) (FIG. 7A, FIG. 7B). Such LNPs can also carry a cargo molecule (e.g., a drug, therapeutic protein or gene-editing complex), which itself can be labelled with chloroalkane for specifically detecting cargo release in various cellular compartments. As depicted in illustrations in FIG. 7A, comparing the penetration of the LNPs themselves to penetration of the cargo (from two separate experiments where LNPs or cargo are chloroalkane-labeled) will provide valuable data describing not only cell penetration, but cargo release extent and kinetics in living cells. As shown in FIG. 7B, dose-dependent suppression of CAPA signal was observed for LNPs formulated with increasing amounts of chloroalkane-functionalized lipid. In addition, parallel curves were also observed for these LNPs in FIG. 7B, demonstrating that CAPA is reporting directly on how much chloroalkane-loaded LNP is accessing the cytoplasm. These results demonstrate that CAPA allows for cytosolic delivery of LNPs in a highly sensitive and quantitative manner.

Collectively, the experiments described above demonstrate the use of CAPA to provide comprehensive cell penetration profiles for a variety of different biomolecules.

The results described herein above, were obtained using the following methods and materials.

Peptide Synthesis and Thioether Stapling.

Peptides were synthesized on Rink Amide resin (0.53 mmol/g) using standard Fluorenylmethyloxycarbonyl (Fmoc) chemistry. For the N-terminal caps, double coupling was required. For HTag-peptides, HTag-COOH (initially obtained from the Chenoweth Lab at University of Pennsylvania, later synthesized by the Kritzer lab) was appended to the N-terminus by reacting 3 eq. with 3 eq. benzotriazol-1-yl-oxytripyrrolidino phosphonium hexafluorophosphate (PyBOP), 3 eq. 1-hydroxybenzotriazole (HOBt), and 6 eq. DIPEA for 1 hour at room temperature. The peptides were globally deprotected and cleaved off the resin by treatment with 94:2.5:2.5:1 (v/v) TFA/ethanedithiol/water/triisopropylsilane for 3 hours. The peptides were triturated in cold diethyl ether and washed two times. The crude pellet was then dissolved in 50:50 acetonitrile/water, and after confirming the identity of the peptide by MALDI-TOF mass spectrometry, was subjected to bis-alkylation conditions as previously shown. All peptides were purified by reserved-phase HPLC on a $C_8$ preparative column. Purity of the final product was confirmed on a $C_{18}$ analytical column.

CAPA

Figure 3A:
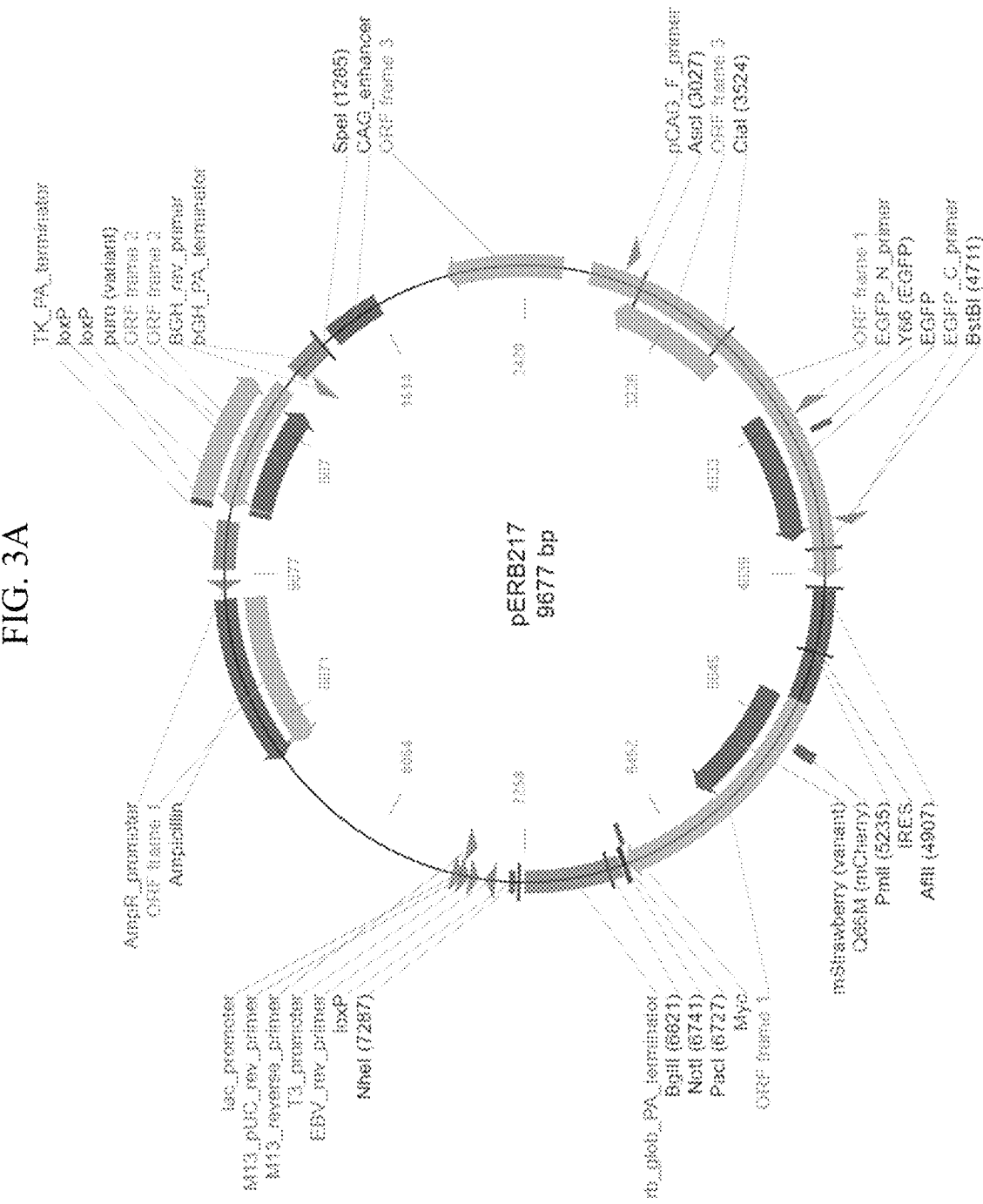
FIG. 3A provides a schematic of the pERB217 plasmid used by Chenoweth et al. to generate the HeLa expressing construct Halo-GFP-Mitochondrial targeted (Mito.)+ mCherry-dihydrofolate reductase (DHFR).
Figure 3B:
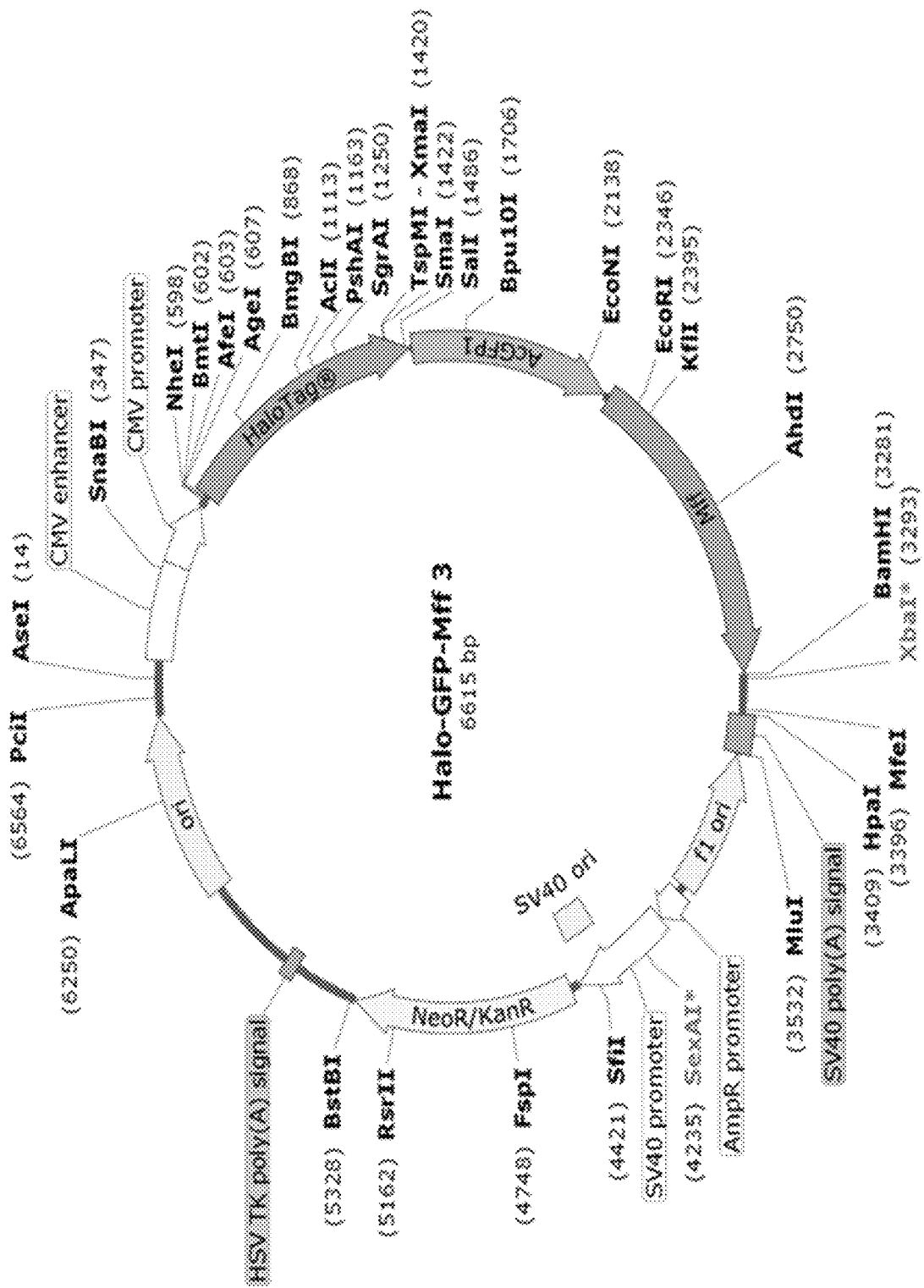
FIG. 3B provides a schematic of the Halo-GFP-mitochondrial fission factor (Mff) construct.

Halo-GFP-Mitochondrial targeted (Mito.)+mCherry-dihydrofolate reductase (DHFR) HeLa cells were obtained from the Chenoweth Lab as described by (Ballister et al., Nat. Commun. 2014. 5, 1-9), which is incorporated herein by reference. The expression vector used for the incorporation of GFP-Haloenzyme is shown at FIG. 3. Cells were cultured using DMEM+10% FBS+1% Pen/Strep+1 µg/mL puromycin. For experiments, cells were seeded in a 24-well plate the day before at $1.0 \times 10^5$ cells/well. Materials for cell culture were purchased from Thermo Scientific.

Cells were rinsed 1× with PBS, then treated with peptides in acidified Opti-MEM (0.15% 6N HCl) for 4 hours. Media was aspirated and cells were washed for 30 min with phenol red-free DMEM+10% FBS+1% pen/strep. Cells were chased with 5 µM HTag-TAMRA (Promega) in phenol red-free DMEM+10% FBS+1% pen/strep for 30 min. Cells were washed for 15 min with phenol red-free DMEM+10% FBS+1% pen/strep. Cells were rinsed once with phosphate buffered saline (PBS), then trypsinized and transferred to 1.5 mL Eppendorf tubes. Cells were pelleted and washed twice with PBS. Cell pellet was resuspended in 250 µL of PBS and 200 µL were transferred to 96-well plate for flow cytometry analysis. Data was gated for live cells measuring 10,000 cells per sample. Mean fluorescence intensity was obtained in the Yellow channel for HTag-TAMRA, and data was normalized. Background yellow fluorescence was observed both by flow cytometry and microscopy due to the constituent expression of mCherry-DHFR, but the signal observed for HTag-TAMRA-treated cells was 10-fold higher than background.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCES

1. Stanzl, E. G., Trantow, B. M., Vargas, J. R. & Wender, P. A. Fifteen Years of Cell-Penetrating, Guanidinium-Rich Molecular Transporters: Basic Science, Research Tools, and Clinical Applications. *Acc. Chem. Res.* 46, 2944-2954 (2013).
2. Wender, P. A., Mitchell, D. J., Pattabiraman, K., Pelkey, E. T., Steinman, L. & Rothbard, J. B. The design, synthesis, and evaluation of molecules that enable or enhance cellular uptake: Peptoid molecular transporters. *Proc. Natl. Acad. Sci. USA* 97, 13003-13008 (2000).
3. Futaki, S., Suzuki, T., Ohashi, W., Yagami, T., Tanaka, S., Ueda, K. & Sugiura, Y. Arginine-rich peptides: an abundant source of membrane-permeable peptides having potential as carriers for intracellular protein delivery. *J. Biol. Chem.* 276, 5836-5840 (2001).
4. Derossi, D., Joliot, A., Chassaing, G. & Prochiantz, A. The Third Helix of the Antennapedia Homeodomain Translocates Through Biological-Membranes. *J. Biol. Chem.* 269, 10444-10450 (1994).
5. Derossi, D., Calvet, S., Trembleau, A., Brunissen, A., Chassaing, G. & Prochiantz, A. Cell internalization of the third helix of the antennapedia homeodomain is receptor-independent. *J. Biol. Chem.* 271, 18188-18193 (1996).
6. Appelbaum, J. S., LaRochelle, J. R., Smith, B. A., Balkin, D. M., Holub, J. M. & Schepartz, A. Arginine Topology Controls Escape of Minimally Cationic Proteins from Early Endosomes to the Cytoplasm. *Chem. Biol.* 19, 819-830 (2012).
7. Qian, Z., Martyna, A., Hard, R. L., Wang, J., Appiah-Kubi, G., Coss, C., Phelps, M. A., Rossman, J. S. & Pei, D. Discovery and Mechanism of Highly Efficient Cyclic Cell-Penetrating Peptides. *Biochemistry* 55, 2601-2612 (2016).
8. Medina, S. H., Miller, S. E., Keim, A. I., Gorka, A. P., Schnermann, M. J. & Schneider, J. P. An Intrinsically Disordered Peptide Facilitates Non-Endosomal Cell Entry. *Angew. Chem. Int. Ed.* 55, 3369-3372 (2016).
9. Qian, Z., LaRochelle, J. R., Jiang, B., Lian, W., Hard, R. L., Selner, N. G., Luechapanichkul, R., Barrios, A. M. & Pei, D. Early Endosomal Escape of a Cyclic Cell-Penetrating Peptide Allows Effective Cytosolic Cargo Delivery. *Biochemistry* 53, 4034-4046 (2014).
10. Bird, G. H., Mazzola, E., Opoku-Nsiah, K., Lammert, M. A., Godes, M., Neuberg, D. S. & Walensky, L. D. Biophysical determinants for cellular uptake of hydrocarbon-stapled peptide helices. *Nat. Chem. Biol.* 12, 845-852 (2016).
11. LaBelle, J. L., Katz, S. G., Bird, G. H., Gavathiotis, E., Stewart, M. L., Lawrence, C., Fisher, J. K., Godes, M., Pitter, K., Kung, A. L. & Walensky, L. D. A stapled BIM peptide overcomes apoptotic resistance in hematologic cancers. *J. Clin. Invest.* 122, 2018-2031 (2012).
12. Edwards, A. L., Wachter, F., Lammert, M., Huhn, A. J., Luccarelli, J., Bird, G. H. & Walensky, L. D. Cellular Uptake and Ultrastructural Localization Underlie the Pro-apoptotic Activity of a Hydrocarbonstapled BIM BH3 Peptide. *ACS Chem. Biol.* 10, 2149-2157 (2015).
13. Chang, Y. S., Graves, B., Guerlavais, V., Tovar, C., Packman, K., To, K.-H., Olson, K. A., Kesavan, K., Gangurde, P., Mukherjee, A., Baker, T., Darlak, K., Elkin, C., Filipovic, Z., Qureshi, F. Z., Cai, H., Berry, P., Feyfant, E., Shi, X. E., Horstick, J., Annis, D. A., Manning, A. M., Fotouhi, N., Nash, H., Vassilev, L. T. & Sawyer, T. K. Stapled alpha-helical peptide drug development: A potent dual inhibitor of MDM2 and MDMX for p53-dependent cancer therapy. *Proc. Natl. Acad. Sci. USA* 110, E3445-E3454 (2013).
14. Peraro, L., Zou, Z., Makwana, K. M., Cummings, A. E., Ball, H. L., Yu, H., Lin, Y.-S., Levine, B. & Kritzer, J. A. Diversity-Oriented Stapling Yields Intrinsically Cell-Penetrant Inducers of Autophagy. *J. Am. Chem. Soc.* (2017). doi:10.1021/jacs.7b01698
15. Muppidi, A., Doi, K., Edwardraja, S., Drake, E. J., Gulick, A. M., Wang, H.-G. & Lin, Q. Rational Design of Proteolytically Stable, Cell-Permeable Peptide-Based Selective Mc1-1 Inhibitors. *J. Am. Chem. Soc.* 134, 14734-14737 (2012).
16. Friedman Ohana, R., Kirkland, T. A., Woodroofe, C. C., Levin, S., Uyeda, H. T., Otto, P., Hurst, R., Robers, M. B., Zimmerman, K., Encell, L. P. & Wood, K. V. Deciphering the Cellular Targets of Bioactive Compounds Using a Chloroalkane Capture Tag. *ACS Chem. Biol.* 10, 2316-2324 (2015).
17. Bradner, J. E., West, N., Grachan, M. L., Greenberg, E. F., Haggarty, S. J., Warnow, T. & Mazitschek, R. Chemical Phylogenetics of Histone Deacetylases. *Nat. Chem. Biol.* 6, 238-243 (2010).
18. Rix, U., Hantschel, O., DUrnberger, G., Remsing Rix, L. L., Planyaysky, M., Fernbach, N. V., Kaupe, I., Bennett, K. L., Valent, P., Colinge, J., Köcher, T. & Superti-Furga, G. Chemical proteomic profiles of the BCR-ABL inhibitors imatinib, nilotinib, and dasatinib reveal novel kinase and nonkinase targets. *Blood* 110, 4055-4063 (2007).
19. Ballister, E. R., Aonbangkhen, C., Mayo, A. M., Lampson, M. A. & Chenoweth, D. M. Localized light induced protein dimerization in living cells using a photocaged dimerizer. *Nat. Commun.* 5, 5475 (2014).
20. Stanzl, E. G., Trantow, B. M., Vargas, J. R. & Wender, P. A. Fifteen Years of Cell-Penetrating, Guanidinium-Rich Molecular Transporters: Basic Science, Research Tools, and Clinical Applications. Acc. Chem. Res. 46, 2944-2954 (2013).
21. Walensky, L. D. & Bird, G. H. Hydrocarbon-Stapled Peptides: Principles, Practice, and Progress. J. Med. Chem. 57, 6275-6288 (2014).
22. Murrey, H. E., Judkins, J. C., am Ende, C. W., Ballard, T. E., Fang, Y., Riccardi, K., Di, L., Guilmette, E. R., Schwartz, J. W., Fox, J. M. & Johnson, D. S. Systematic Evaluation of Bioorthogonal Reactions in Live Cells with Clickable HaloTag Ligands: Implications for Intracellular Imaging. J. Am. Chem. Soc. 137, 11461-11475 (2015).

What is claimed is:

1. A method for quantifying cell penetration of an agent, the method comprising:
   (a) contacting a cell expressing a chloroalkane dehalogenase haloenzyme comprising SEQ ID NO: 1 with an agent conjugated to chloroalkane in a first step;
   (b) contacting the cell with chloroalkane conjugated to a fluorescent detectable moiety in a second step following step (a); and
   (c) measuring the relative amount of cellular fluorescence following steps (a) and (b) by detecting a fluorescent signal from the detectable moiety, wherein the fluorescent signal indicates the amount of free haloenzyme, which is inversely proportional to the signal associated with binding of the haloenzyme to the agent conjugated to chloroalkane in the cell, and wherein the signal quantifies the cell penetration of the agent conjugated to chloroalkane.

2. The method of claim 1, wherein the agent is selected from the group consisting of a bacterium, nucleic acid molecule, polypeptide, peptide, small molecule, viral particle, nanoparticle, and macromolecule.

3. The method of claim 1, wherein the detectable moiety is a cell permeable fluorescent tag.

4. The method of claim 1, wherein the cell expresses a fusion protein comprising chloroalkane dehalogenase haloenzyme fused to a detectable reporter that localizes the fusion protein to one or more of the nucleus, mitochondria, or cytoplasm.

5. The method of claim 4, wherein the signal from the detectable moiety co-localizes with the signal from the detectable reporter.

6. The method of claim 4, wherein the cell is a eukaryotic or prokaryotic cell.

7. The method of claim 1, wherein the agent comprises a free amine group and is conjugated with chloroalkane by covalently linking the free amine group and a chloroalkane ligand.

8. The method of claim 7, wherein the free amine group is conjugated to the chloroalkane ligand in the presence of a coupling agent.

9. The method of claim 8, wherein the coupling agent is benzotriazol-1-yl-oxytripyrrolidino-phosphonium hexafluorophosphate (PyBOP).

* * * * *